(12) United States Patent
Benner et al.

(10) Patent No.: US 10,745,728 B1
(45) Date of Patent: *Aug. 18, 2020

(54) APPLICATIONS FOR BIVERSAL NUCLEOSIDE ANALOGS

(71) Applicants: Steven A Benner, Gainesville, FL (US); Hyo-Joong Kim, Gainesville, FL (US); Zunyi Yang, Gainesville, FL (US)

(72) Inventors: Steven A Benner, Gainesville, FL (US); Hyo-Joong Kim, Gainesville, FL (US); Zunyi Yang, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,766

(22) Filed: Aug. 27, 2018

Related U.S. Application Data

(63) Continuation-in-part of application No. 15/377,236, filed on Dec. 13, 2016, now Pat. No. 10,059,735.

(60) Provisional application No. 62/267,382, filed on Dec. 15, 2015, provisional application No. 62/655,998, filed on Apr. 11, 2018.

(51) Int. Cl.
| | | |
|---|---|---|
| *C07H 19/00* | (2006.01) | |
| *C07H 21/00* | (2006.01) | |
| *C12P 19/34* | (2006.01) | |
| *C12Q 1/686* | (2018.01) | |
| *C07H 19/04* | (2006.01) | |
| *C07H 21/02* | (2006.01) | |
| *C07H 21/04* | (2006.01) | |

(52) U.S. Cl.
CPC .............. *C12P 19/34* (2013.01); *C12Q 1/686* (2013.01); *C07H 19/04* (2013.01); *C07H 21/02* (2013.01); *C07H 21/04* (2013.01)

(58) Field of Classification Search
None
See application file for complete search history.

(56) References Cited

U.S. PATENT DOCUMENTS 6,600,028 B1 * 7/2003 Brown ................. C07D 498/16
435/7.2
7,014,994 B1 * 3/2006 Barany ................ C12Q 1/6816
435/183

OTHER PUBLICATIONS

Dobosy, Joseph R., et al. "RNase H-dependent PCR (rhPCR): improved specificity and single nucleotide polymorphism detection using blocked cleavable primers." BMC biotechnology 11.1 (2011): 80.*

* cited by examiner

*Primary Examiner* — Patrick T Lewis

(57) ABSTRACT

This invention relates to the use of analogs of purines that have two tautomeric forms, one formally complementary to thymidine, the other formally complementary to cytidine, and analogs of pyrimidines that have two tautomeric forms, one formally complementary to guanosine, the other formally complementary to adenosine. These uses include the polymerase chain reaction amplification of targets having polymorphisms in primer binding sites and ligation.

16 Claims, 24 Drawing Sheets

Specification includes a Sequence Listing.

APPLICATIONS FOR BIVERSAL NUCLEOSIDE ANALOGS

CROSS REFERENCE TO RELATED APPLICATIONS

This application is a continuation-in-part of non-provisional U.S. patent application Ser. No. 15/377,236, currently pending, which was filed 13 Dec. 2016, for "Nucleoside Heterocycle that Binds to Both Thymidine and Cytidine". It also claims the benefit of provisional U.S. Patent Application 62/655,998 Filed 11 Apr. 2018, for "Applications for Biversal Nucleoside Analogs".

STATEMENT OF RIGHTS TO INVENTIONS MADE UNDER FEDERALLY-SPONSORED RESEARCH

This work was supported by the National Institute of Allergy and Infectious Diseases of the National Institutes of Health under Award Number R21A1133567 and the National Institute of General Medical Sciences of the National Institutes of Health under Award Numbers R41GM115130 and R42GM115130. The government has certain rights in the invention.

The Names of Parties to a Joint Research Agreement

Not applicable.

Incorporation by Reference of Material Submitted on a Compact Disk

None.

BACKGROUND OF THE INVENTION

1. Field of the Invention

The field of this invention is nucleic acid chemistry, which concerns DNA, RNA, and their analogs, more specifically the field that covers processes for binding to DNA and RNA molecules to form duplexes. More specifically, it relates to binding between nucleic acid analogs of the instant invention and target olionticicotides whose sequence is not precisely defined. Further, this invention relates to nucleotide analogs that, when embedded in an oligonucleotide probe, pair with sites in a target oligonucleotide that hold an imprecisely defined, and possibly unknown, pyrimidine. This invention further relates to the manipulation of complexes formed when oligonucleotides containing these analogs bind to such targets.

2. Deseription of the Related Art

Binding of oligonucleotide probes (DNA or RNA, or collectively, xNA) to tarot oligonucleotides is widely used in the art to detect the presence of the target in samples. The detection architecture can involve simple binding. Alternatively, the detection architecture can use binding as the first step of a process, such as primer extension or ligation. In many cases of the instant invention, these processes involve enzymes.

In many binding procedures havinn practical value, the precise sequenceof the target oligonucleotide may not be defined, or may not even be known. For example, the genetic variability of rapidly evolving RNA viruses, such as HIV, causes these RNA binding targets to have sites that contain one of the two pyrimidines (uracil or cytosine, U or C), or one of the two purines (adenine or guanine, A or G). These weaken the binding of the probe to these sequences, leading to less efficient detection. Here, this weakening can cause assays to underestimate the prevalence of the virus in a population, the load of the virus in a patient, or even the presence of the virus in a patient. Mutations in regions that bind to pruners and probes lower their affinities and eventually preventing their binding entirely (1-3). This problem is important to develop assays to detect pathogenic viruses having genetic variability (4,5).

One strategy to manage this variability simply creates multiple primers that perfectly match all conceivable variants in a population of targets (6), either by explicit synthesis of multiple primers, or by using mixtures or phosphoramidites when adding a nucleotide at an ambiguous site (7). However, with each level of added diversity, the concentration of the effective binder drops, and the amount of off-target amplification increases. Both reduce assay sensitivity. Further, even with these strategies, medically relevant drug resistance mutations embedded in a segment of the gene containing irrelevant variability can rapidly become difficult to detect (3).

An alternative strategy well-known in the art uses a "universal nucleobase", a nucleotide analog that can pair with all natural nucleobases in its binding (8,9). A large literature covers many universal nucleobase designs (10-12). In practice, inosine is often used as a universal base, notwithstanding some problematic aspects of its behavior (13-14). Because of these, no single analog can be considered to be truly universal (15,16).

True universality is, however, not always needed (or en desired) for biological applications. First, if too many universal nucleotides are added to a probe, the resulting molecule may have too many places to bind off-target in a complex DNA sequence background. Further, when seeking to manage a naturally divergent sequence, evolutionary analyses often find that transition mutations (replacing a purine by a purine, or a pyrimidine by a pyrimidine) are more common than transversions (replacing a purine by a pyrimidine, or a pyrimidine by a purine) in coding and non-coding regions (17,18). In these cases, "biversality" (binding to either purine, or to either pyrimidine, but not to both purines and pyrimidines) may be preferred over universality, managing the more common ambiguity without creating excessive off-target binding.

Tautomerism is one strategy to create biversality. For example, Brown and his coworkers made candidate biversals by exploiting the tautomerism of oximes (19). Their pyrimidine biversal used the oxime-alkoxyamine tautomerization of N6-methoxycytidine (20); here, the oxime tautomer is hydrogen-bond complementary to A, while the enamine tautomer is complementary to G (FIG. 1). Their corresponding purine biversal exploited oxime-alkoxyamine tautomerization in a purine ring with N6-methoxydiaminopurine (21,22); the oxime tautomer is hydrogen-bond complementary to C, while the alkoxyamine tautomer is complementary to T (FIG. 2).

In Brown's pyrimidine biversal P, the methoxy group is "tied back" in a ring. While not wishing to be bound by theory, this prevents rotation that would allow it to swing to obstruct Watson-Crick pairing (FIG. 1). Because of the nitrogen at position 7, purines themselves do not offer any ready position to tie back the exocyclic N—O unit (FIG. 2, left). Thus, in the classical purine biversal systems of Brown, the melting temperatures are lower, presumably because the methoxy group in the incorrect conformation interferes with hydrogen bonding to the Watson-Crick complement.

Brief Summary of the Invention

In principle, a tricyclic analog based on a 7-deazapurine, whose carbon is a point of attachment to the ring system, should have electronic properties similar to the conformationally flexible oxime. This compound has been discussed in the literature by Brown and his coworkers, who attempted to make a purine analog, but without success (23,24).

U.S. Ser. No. 15/377,236, for which this is a continuation in part, is incorporated in its entirety by reference, in particular for its synthetic procedure, a procedure that first generated these tricyclic purine biversal compounds. The instant disclosure describes processes that use this biversal, and biversals previously known in the art. This includes processes involving simple binding, where biophysical data are provided with complementary and semi-complementary oligonucleotide targets, the second defined as those where the target has one of two pyrimidines at a site, or one of two purines. It also includes processes comprising PCR amplification that exploit primers containing these biversals, and ligation to detect single nucleotide polymorphisms (SNPs) using probes having various numbers of these biversals.

DETAILED DESCRIPTION OF THE INVENTION

Figure 1:
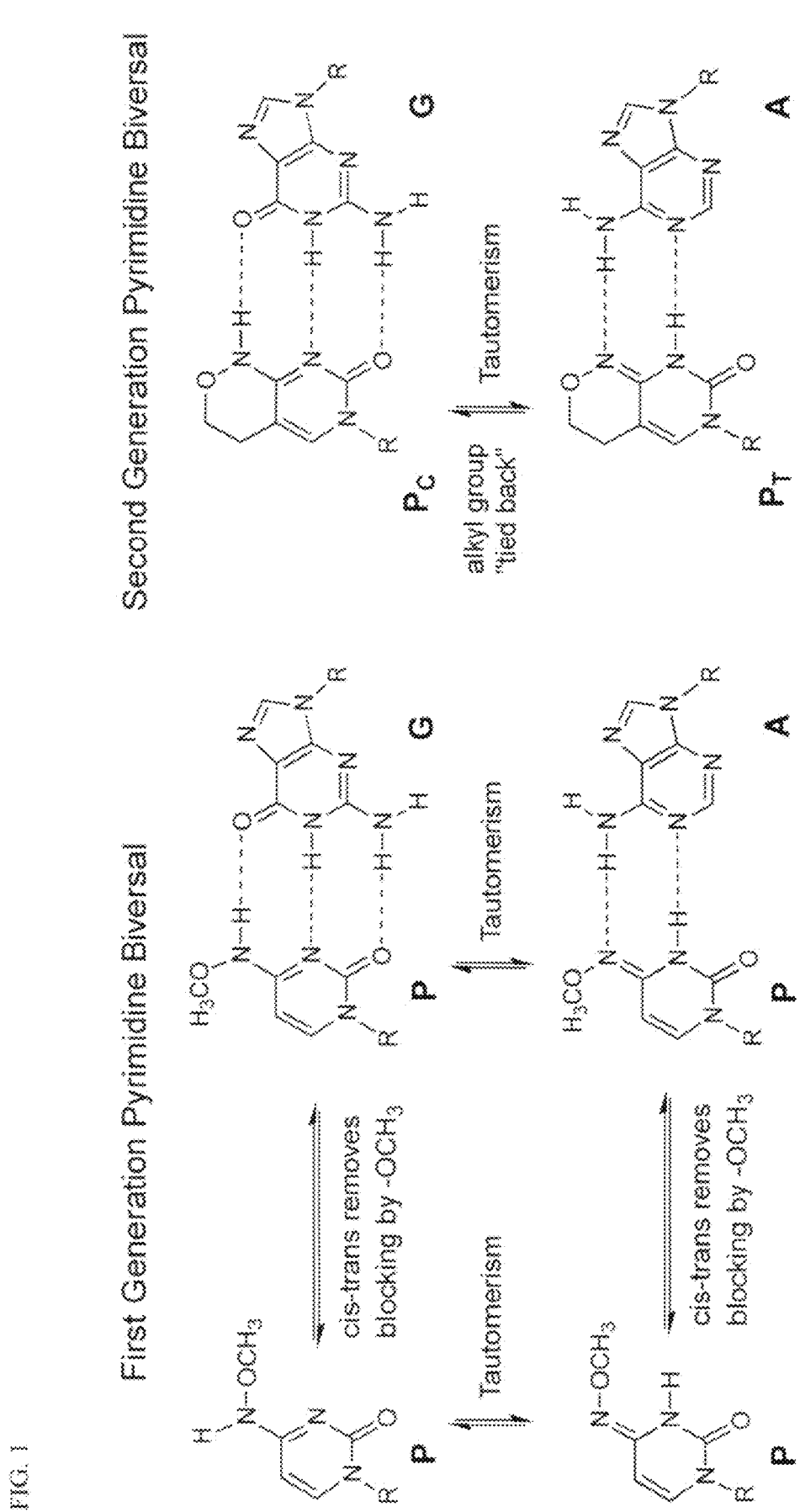
FIG. 1. Two candidate pyrimidine biversal nucleoside analogs that exploit oxime-alkoxyamine tautomerism. The first generation as two conformations of the MeO-group, one that obstructs nucleobase pairing. The second generation biversal ties this group into a ring, preventing the obstruction.
Figure 2:
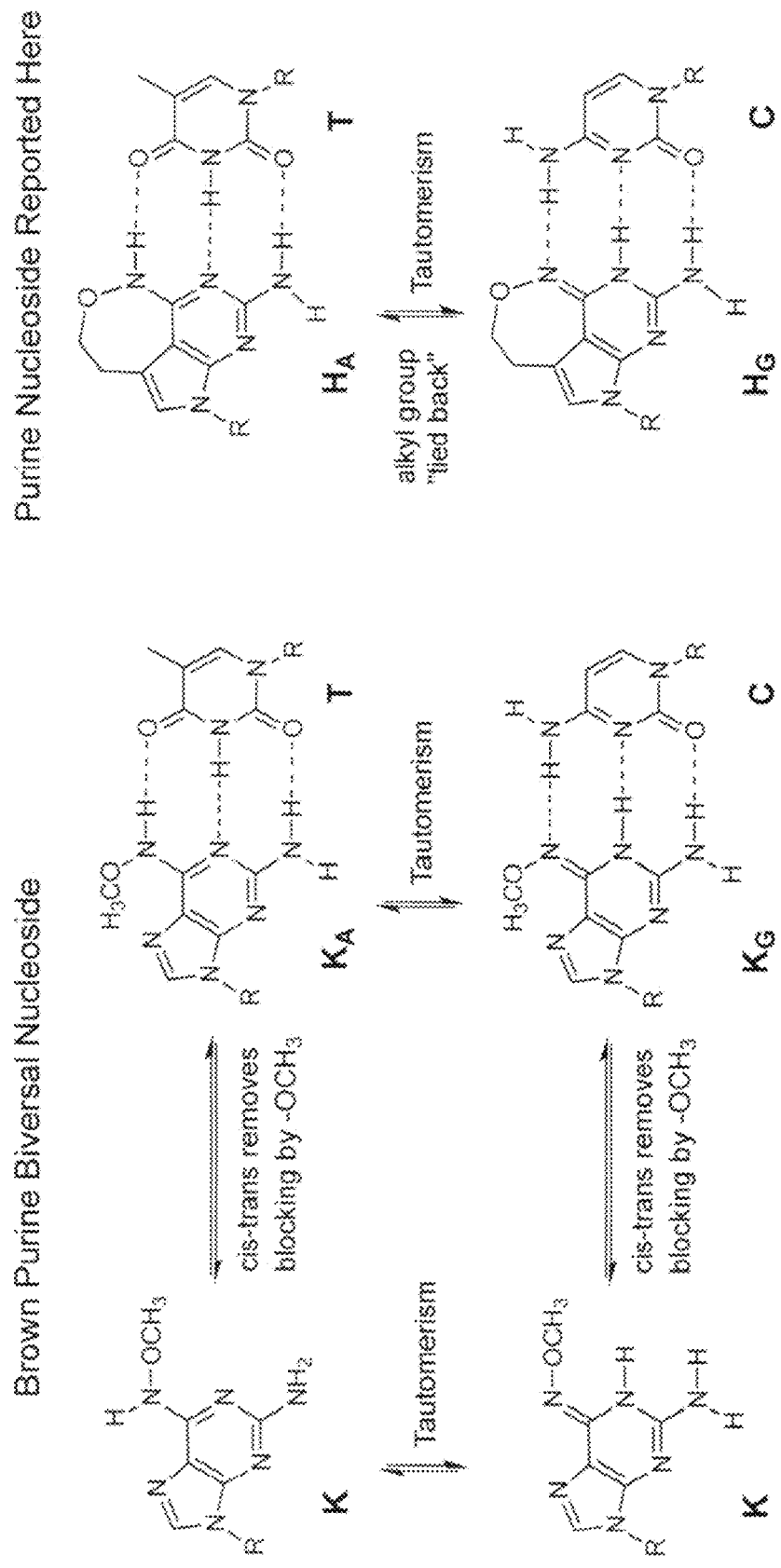
FIG. 2. Two candidate purine biversal nucleosides. In the purine biversal nucleoside reported by Brown (K, left), the appended $CH_3O$ group can adopt a conformation that obstructs nucleobase pairing with either T or C. In the purine "tricyclic" biversal of the instant invention (H, right), this cannot happen that in either of its two tautomeric forms, $H_A$ and $H_G$. However, the additional ring may influence the tautomer ratio.

While not wishing to be bound by theory, Brown's pyrimidine nucleobase theoretically displays biversal behavior because the addition of an oxygen atom to the exocyclic amino group shifts the imine-enamine tautomeric equilibrium (FIG. 1, FIG. 2) (27). Without that oxygen atom, the amino tautomer is strongly favored over the imino tautomer. Thermal denaturation experiments of DNA with Brown's pyrimidine biversal nucleosides show that the "tied-back" bicyclic version was much better than OMe-N6-eytidine, perhaps for the steric reasons theoretically considered above.

Brown considered the possibility of tying back the RO— group in the analogous purine species. However, he was unable to make a tied-back version of the purine biversal.

The successful synthesis ot the "tied back" tricyclic purine oxime 2-(2-Deoxy-b-D-ribofuranosyl)-4-pivaloylamino-2,6,8,9-tetrahydro-7-oxa-2,3,5,6-tetraazabenz[cd]azulene (trivially called H in this specification) reported here allows, for the first time, evaluation of the "oxime tautomerism" strategy to create biversality. Primers containing the purine biversal H primers perform comparably well as perfectly matched standard primers in PCR. They work better than standard primers that are mismatched against mutated targets (by ~5 cycles with multiple mismatches). This H allows more uniform amplification of perfectly matched targets and mutated targets in an evolved virus.

However, thermodynamic measurements suggest that the added ring in H perturbs its tautomeric ratio in favor of the H:T match over the H:C match. This perturbation is reflected in enzymatic pairing with template H, making it behave more like A. This may be useful in PCR amplification, as the preference for H:T matches allows ambiguity in targets to be "resolved" in amplicons in favor of T.

Primers containing H performed competitively with the universal base inosine (I) in many contexts. However, H performed better in ligation assays. We expect this to be its principal application over inosine. H may also be adapted to Taqman-like assays (28), where small numbers of mismatches have large impacts on the outcome.

Single oligonucleotide probes that match ambiguous sites with "universal bases" or "biversal bases" could also replace mixed primers. They might also replace consensus primers that overlook the divergence in the initial PCR priming step, as in PANDAA (Pan Degenerate Amplification and Adaptation) to detect HIV drug-resistance (29). Biversal base-containing primers and probes can also be used in isothermal amplification and other genotyping assays to detect medically relevant SNPs at sites flanked by irrelevant variation.

Multiple ligases were examined and found to work. These include, without limitation, the ligase from *Thermus aquaticus* (Taq), 9°N ligase, Pfu DNA ligase, T4 DNA ligase, Splint R® ligase, and High Fidelity Taq DNA ligase. T4 RNA ligase 2 (from New England Biolabs) was also effective, meaning that the template may be RNA as well as DNA. Likewise, RNA fragments and DNA-RNA chimeras were effective in this ligation. The presently most preferred ligase is Taq ligase. These involved different cofactors, but have as the common element the result of linking, or joining, the two fragments by a phosphodiester bond, creating a covalent DNA molecule that comprises the sequences of both.

As is well know in the art, the ligation architecture describing the ligation of two fragments requires a DNA or RNA temp ate that has two adjacent segments, wherein said first segment is substantially complementary to a donor fragment, and said second segment is substantially complementary to an acceptor fragment, the temperature and buffer must be chosen to provide conditions where the donor fragment binds to the first segment and the acceptor fragment binds to said second segment to form a hybrid complex, and the segment of the template that binds the donor fragment is 5'-adjacent to the segment of the template that binds the acceptor fragment. This is then followed by incubating the hybrid complex with a ligase under conditions where the two fragments become joined by phosphodiester bond. This requires the donor fragment to carry a 5'-phosphate group; the acceptor fragment must have a free 3'-end.

The instant invention has at least one biversal in each of the fragments being ligated. The presently preferred number of biversals is 1, 2, or 3. The presently preferred number of fragments being ligated is two, where the fragments are complementary to two adjacent segments in the template. However, multiple fragments may be ligated on a template that contains multiple adjacent segments.

For primer extension, at least one biversal must be present in the primers being extended. However, an indefinitely large number of biversals may be present. The presently preferred number of biversals is 1, 2. Many polymerases work. The presently preferred polymerases are Taq DNA polymerase, reverse transcriptase, and AmpliTaq Gold DNA polymerase. Since reverse transcriptase works with such primers, the template may be either DNA or RNA.

For PCR, the number of primers is increased. As is well known in the art, PCR increases the number of copies of two complementary DNA target strands by process that comprises: (a) adding one or both of the target strands to an aqueous micture that has a thermostable DNA polymerase and 2'-deoxynucleoside triphosphates that complement each of the nucleotides in the strands. The aqueous mixture also contains two primers, a first primer that is substantially complementary is sequence to a segment at or near the 3'-end of the first DNA strand, and a second primer that is substantially complementary in sequence to a segment at or near the 3'-end of the second DNA strand. In the instant invention, one or both of the primers contains one of the purine tricyclic biversals, with that number depending on how many ambiguous sites are in the target DNA strands. The presently preferred number of tricyclic biversals is determined by the number of ambiguous sites.

Figure 24:
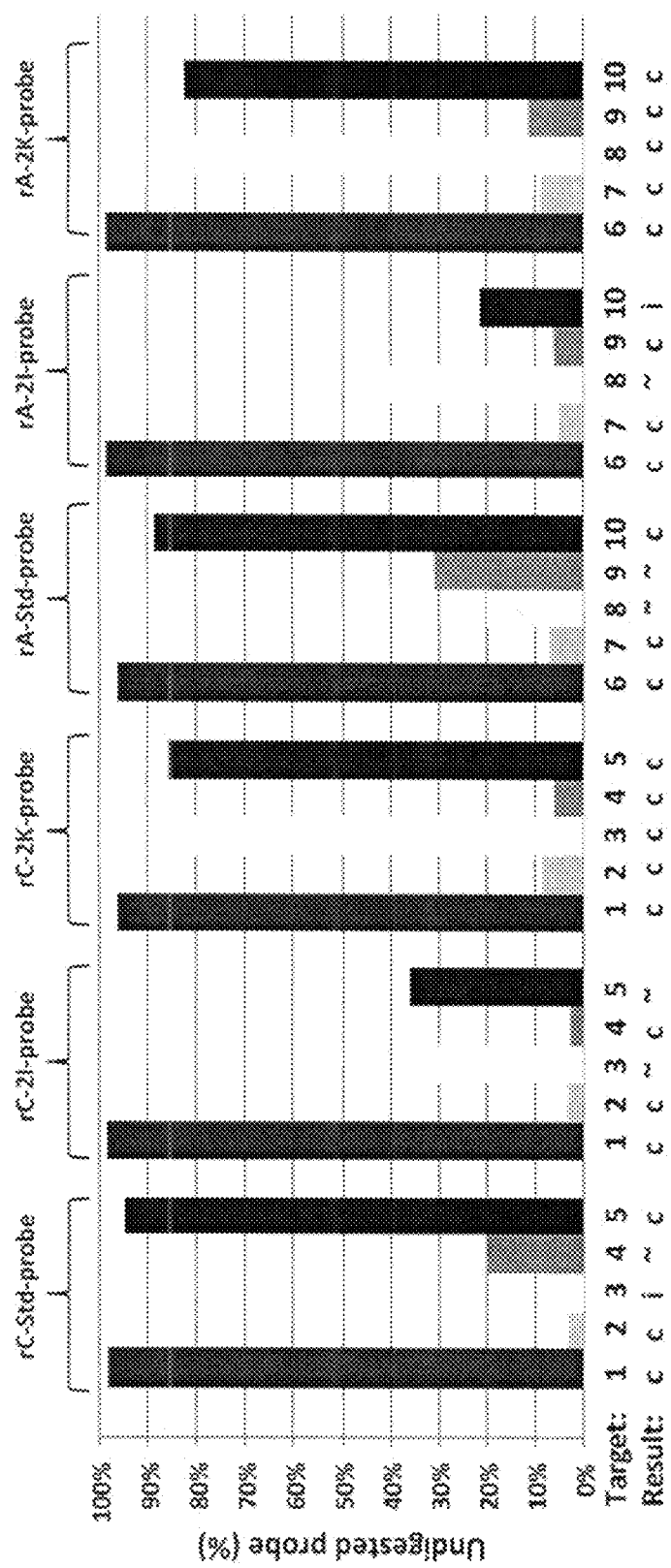
FIG. 24. Results of an assay seeking to identify medically interesting single nucleotide polymorphisms (SNPs) by probing the target with a probe containing a single RNA nucleotide at the SNP site. Here, the probe contains one or more hiversals at the medically uninteresting nearby sites. The Y axis is the fraction undigested by RNase H2. The result is assigned as correct (c), incorrect (i), or undesirably ambiguous (~) when matching the MISs with standard-probe, 2I-probe, or 2K-probe.

To identify medically interesting single nucleotide polymorphisms (SNPs) by probing the target with a probe containing a single RNA nucleotide at the SNP site (FIG. 24). Here, the probe contains one or more biversals at the medically uninteresting nearby sites. The process comprising (a) contacting said target sequence with a probe that is substantially complementary to the target sequence, said probe containing a single ribonucleotide complementary to a nucleotide that might occupy said site, the remainder of the nucleotides in said probe being 2'-deoxyribonucleotides, under conditions where said probe and said target hybridize to form a duplex, and (b) incubating said complex with a ribonuclease H under conditions where the probe is cleaved should the probe ribonucleotide perfectly match the nucleotide in said site, wherein said duplexes contains at least one pyrimidine biversal (P in FIG. 1) or one purine biversal (K or H in FIG. 2), with that number depending on how many ambiguous sites are in the target DNA strands. The presently preferred number of biversals is determined by the number of ambiguous sites. The presently preferred ribonuclease H is ribonuclease H2 (RNase H2).

EXAMPLES

Example 1

Oligonucleotides

Oligonucleotides were synthesized in 1.0 μmol scale using the recommended protocol for an ABI 394 DNA synthesizer, with extended coupling time (10 min) for the tricyclic purine biversal (13). All natural (A, G, C, and T) phosphoramidites were from Glen Research. Oligonucleotides were cleaved from solid support and deprotected by treatment with 0.05 M K2CO3 in MeOH (0.2 mL, 55° C. overnight). The deprotection mixture was diluted with 1 M TEAA (0.4 mL), desalted by Sep-Pak (Waters), and purified by ion exchange HPLC (Dionex DNAPac PA-100 22 ×250 mm Prep column, eluent A=25 mM NaOH+0.1 M NaCl, eluent B=25 mM NaOH+1 M NaCl, from 10% to 50% B in 30 min, flow rate 10 mL/min). The appropriate fractions were collected, neutralized by aqueous acetic acid, desalted by Sep-PaK, and lyophilized. DNA with natural nucleobases only was obtained from Integrated DNA Technologies, Coralville, Iowa.

Melting Temperature Analysis

Oligonucleotides were combined in equimolar concentrations (1 μM) in buffer (0.1 M NaCl, 0.02 M sodium cacodylate pH 7.0). Absorbance of each solution was monitored at 260 nm over a temperature range from 20° C. to 85° C. with a ramp rate of 0.5° C./min. Melting curves were measured on a Shimadzu UV spectrophotometer UV-1800 with a thermal Peltier cell block and temperature probe.

Sanger Sequencing of the PCR Products generated with 3H- and 4H-containing primers Wild type DNA template was amplified by standard primers, 3H- or 4H-containing primers (1 μM of each primer) in 1× AmpliTaq Gold reaction buffer (15 mM Tris-HCl, 50 mM KCl, pH 8.3 at 25° C.), MgCl$_2$ (3 mM), dNTPs (each 0.2 mM), and 2.5 units of Hot Start AmpliTaq Gold DNA polymerase (5 U/μL, ABI, total 25 μL). PCR: one cycle 95° C. for 10 min; followed by 35 cycles (95° C. for 10 s, 50° C. for 30 s, 72° C. for 30 s); finally 72° C. for 5 min. Upon completion, samples (10 μL) were mixed with 6× agarose loading dye (2 μL, Promega), and analyzed on 3% agarose gel.

PCR products (2 μL) were cloned (pCRTM4-TOPO® using TOPO TA Cloning Kit (Invitrogen) and transforined into One Shot® TOP10 competent cells following manufacturer's instruction, Blue-white screens gave 32 colonies that were sequenced (BioBasic).

Amplification Efficiency of 3H-, 4H-, and 4K-Containing Primers Using Real-Time PCR Wild type templates (3×10⁶ and 3×10⁴ copies of Wt-90) and dweTgent templates (3×10⁶ and 3×10⁴ copies of Div4-90) were amplified ((1×AmpliTaq Gold, 15 mM Tris-HCl, 50 mM KCl, pH 8.3 at 25° C.), MgCl$_2$ (3 mM), dNTPs (each 0.2 mM), Hot Start AmpliTaq Gold DNA polymerase (2.5 units, 5 U/μL, ABI). and EvaGreen® the (0.2×Biotium) using four types of primers (standard, 3H-containing primer, 4H-containing primer, 4K-containinia primer, Table 2) respectively. PCRs and non-template controls (NTC) were performed under identical conditions for each primer at 95° C. for 8 min, followed by 40 cycles (95° C. for 10 s, 50° C. for 30 s, 72° C. for 30 s) in the Roche LightCycler® 480 real-time PCR system. LightCycler® 480 software calculates threshold cycle (Ct) and Tm for each. Each assay was repeated twice. Upon completion of PCR, each sample (10 μL) was mixed with 6× agarose loading dye (2 μL, Promega) and analyzed on agarose gel (3%) electrophoresis.

Example 2

Ligation

General Protocol for the Ligation Assay

Each ligation mix had a $^{32}$P-labelled acceptor probe (100 nM), one donor probe (5'-phosphorylated, 100 nM), and target (100 nM) in 1× ligation buffer. Mixtures (15 μL) were first heated (90° C., 1 min) in a Bio-Rad Thermal Cycler, cooled (to 45° C. unless stated otherwise, 0.2° C./s). Ligase (Taq 40 U/reaction, 5 μL in 1× ligation buffer) was added to (final volume 20 μL). Mixtures (20 μL) were incubated (45° C. for 5, 20, or 60 min. Aliquots (7 μL) were quenched (7 μL loading dye with 10 mM EDTA, 95% of formamide), and the products and probes were resolved by PAGE (20%, 7 M urea).

Nucleoside and Oligonucleotide Synthesis

Figure 3:
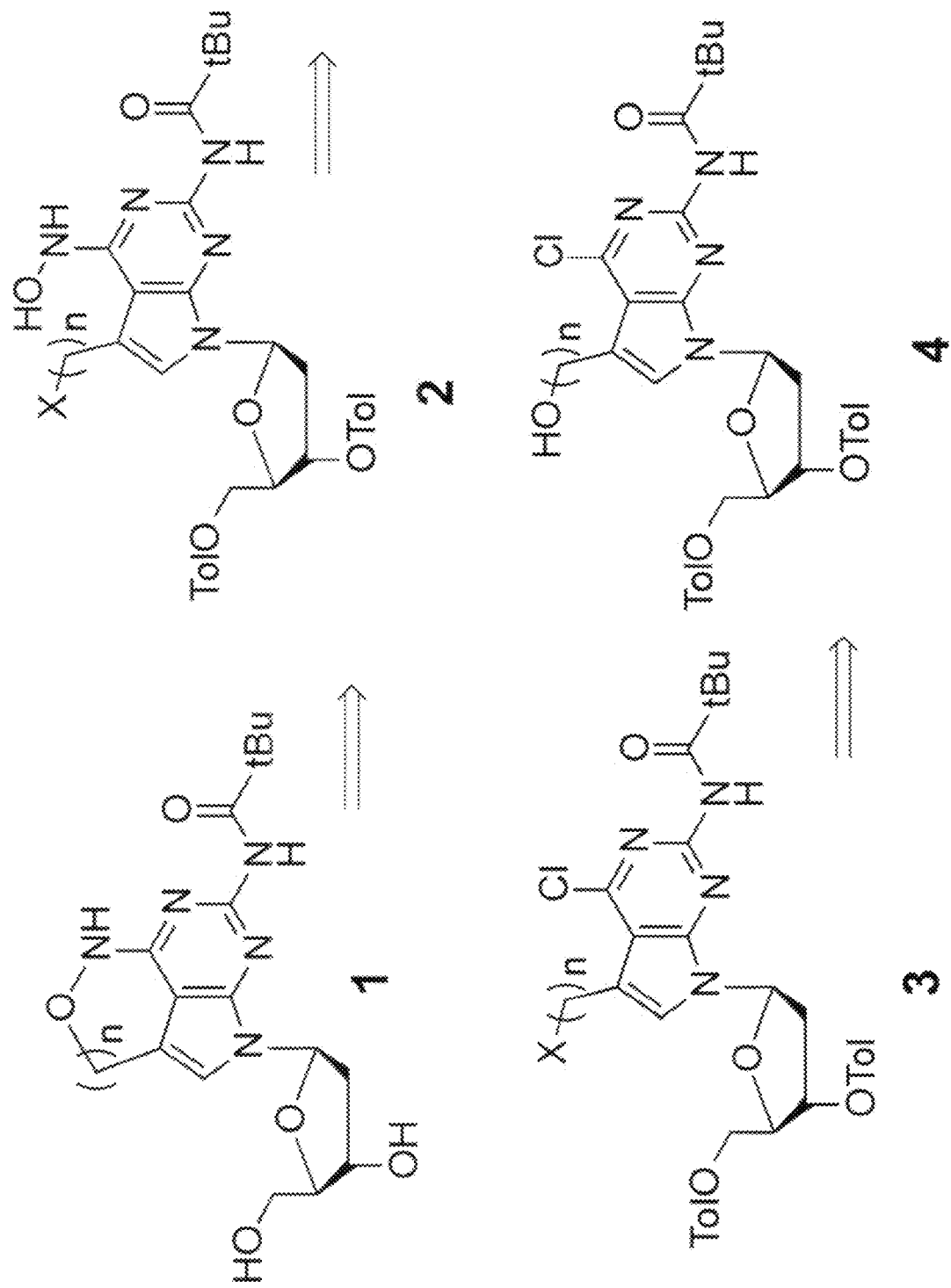
FIG. 3. Retrosynthetic strategy for biversal tricyclic purine nucleosides with different numbers of atoms in the third ring.

The synthesis plan is disclosed in U.S. Ser. No. 15/377,236. That ring could have either one (n=1) or two (n=2) $CH_2$ units. In either, the leaving group for compound 3 might arise from an alcohol in 4, available from a vinyl unit if n=1 and from an allyl unit if n=2 (FIG. 3). Both were made, but only the tosylate and mesylate with n=2 proved to be satisfactory.

Figure 4:
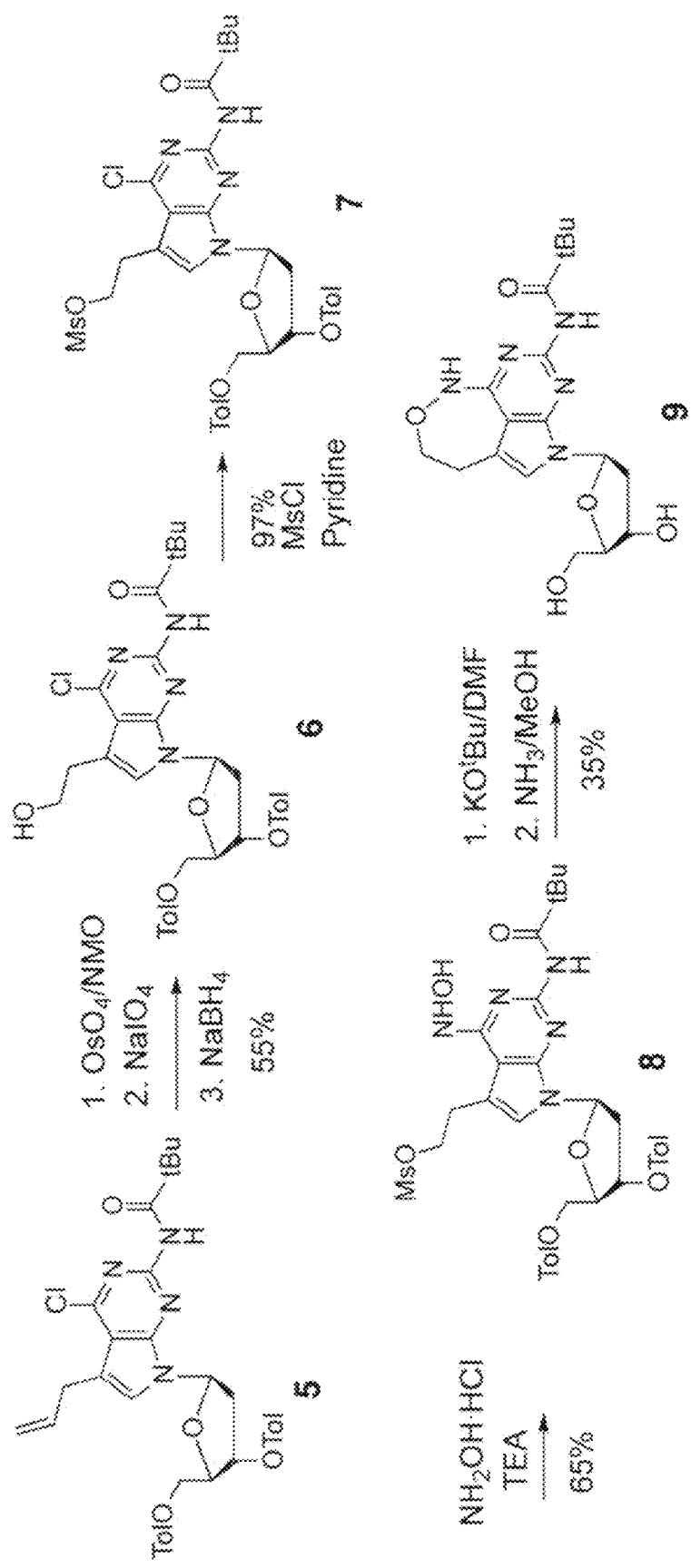
FIG. 4. The first part of the procedure to synthesize the biversal tricylic purine nucleoside 10 and its phosphoramidite 13.

Thus, a new synthesis began by converting 5 (FIG. 4) to an alcohol that was mesylated to give 7 (25). The chloride in 7 was displaced by hydroxylamine followed by cyclization 8 with potassium tert-butoxide in DMF; the reaction failed when THF was used as solvent.

Figure 5:
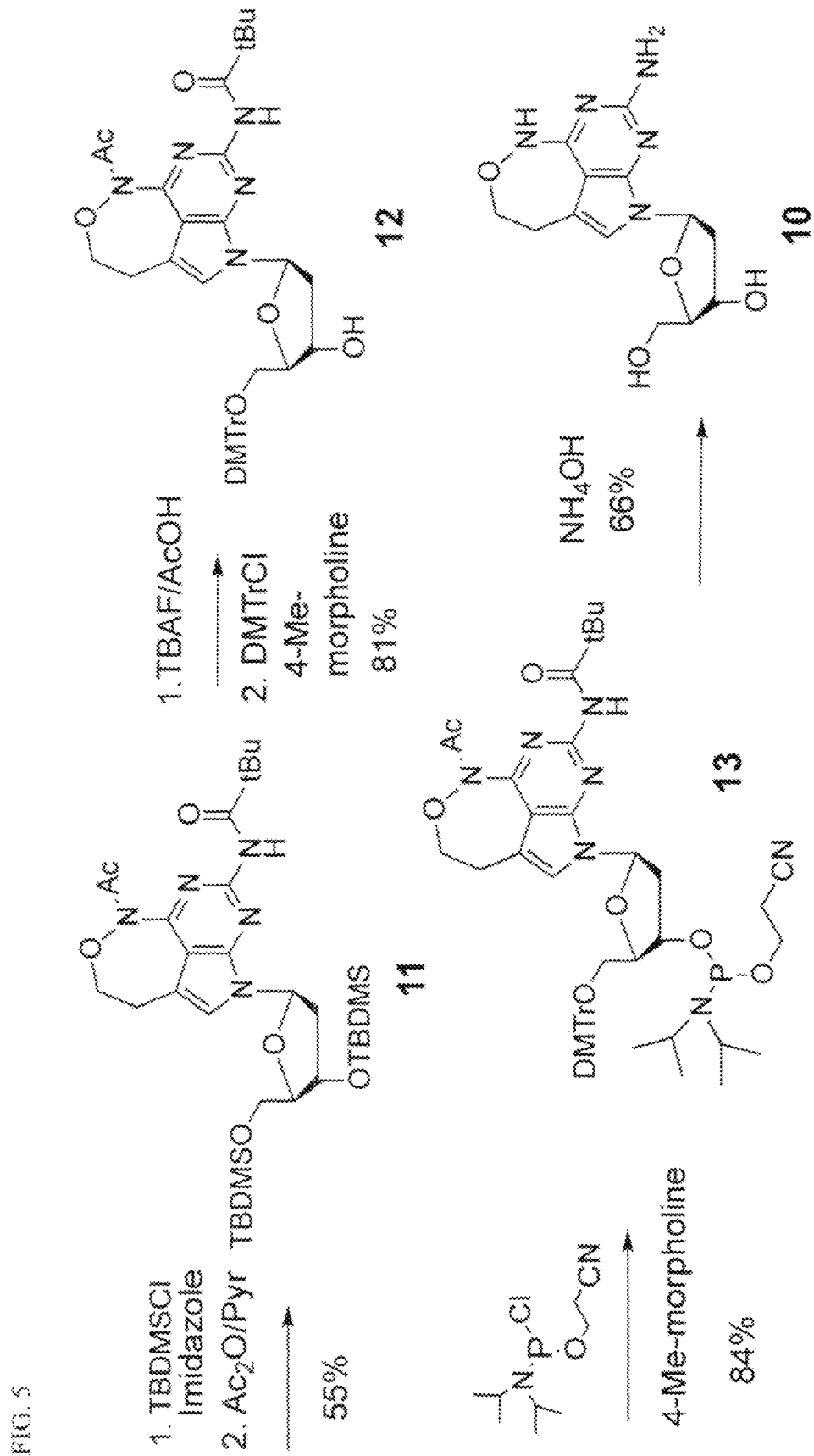
FIG. 5. The second part of the procedure to synthesize the biversal tricylic purine nucleoside 10 and its phosphoramidite 13.

The product from cyclization, after being purified by chromatography, was treated with methanolic $NH_3$ at 25° C. to give analytically pure 9, confirmed by $^1H$ and $^{13}C$ NMR, and high-resolution as spectrometry (HRMS). Removal of the pivaloyl group in $NH_3$ at 55° C. gave deprotected tricyclic nucleoside 10 (FIG. 5), confirmed by NMR and HRMS. The UV of 10 shows two maxima (270, 301 nm), assigned to the imine and alkoxyamine tautomers.

Protected phosphoramidite 13 made from 9 (FIG. 5) was used for solid phase DNA synthesis. Deprotection in $NH_3$ at 55° C. overnight was not complete. Deprotection was achieved by $K_2CO_3$ (0.05 M) in MeOH (55° C. overnight) to give oligonucleotides with two to four tricyclic purine nucleosides (H) easily resolved by HPLC (Tables 1-4).

Example 3

Duplex Formation

Thermal Stability

For hybridization, complementary oligos with all possible nucleotides at the biversal pairing site were synthesized. For comparison, oligos containing first-generation purine biversal nucleobase 2-amino-6-methoxyaminopurine (K, Glen Research) and natural A and G in the same position were synthesized (Table 1).

The first set of denaturation experiments (Table 1) reproduce Brown's with his first generation purine biversal K. Consistent with his reports, K showed biversality and specificity. The $T_m$ values of duplexes containing two or three K:T pairs were only slightly higher than those with K:C pairs. The values of duplexes with purine:purine K:G and K:A mismatches were lower; the $\Delta T_m$ was ~2° C. per substitution. $T_m$ values of K:C and K:T were much lower than the values of duplexes containing the natural pairs (G:C and A:T), also consistent Brown's reports.

H was biophysically better by some metrics. Thus, the $T_m$ of duplexes containing H:T pairs were almost the same as those duplexes containing A:T pairs, which were higher than the same duplexes with K:T pairs by ~2.3° C. per substitution. The H:C pair had $T_m$s similar to those with K:C pairs. However, context variability was large. In duplexes with two central X:Y pairs, the $T_m$ with H:C pairs was 3° C. higher than with K:C pairs, while in duplex with two end X:Y pairs, the $T_m$ of H:C pairs was 2° C. lower than the $T_m$ of K:C pairs. With three substitutions pairing with C, no preference of H over K was seen (Table 1).

H displayed less biversality in these studies. The difference in $T_m$s of K paired with T versus C was only ~0.7° C. per substitution, T being the preferred partner for H. In contrasts, the preference of H for T over C was ~3° C. per substitution. This implies that H resembles adenine more than guanine. This parallels its enzymatic properties (see below); H is more "enamine" than "oxime".

Example 4

SNP Detection by Rnase H2 Cleavage

Chimeric ribo-DNA probes 30 nt's in length (rC-Std, rC-2I, OR rC-2K probe) were hybridized with either a perfectly matched (g-mut-1) template or templates containing mismatches (a-wt-90 or c-mut-2). The ribo-DNA probe and target mixtures (17 μL) were all incubated at 90° C. for 1 min and cooled to 55° C. (0.2° C./s), held at least for 2 min, mixtures were then incubateded to the appropriate temperature (45 to 70° C.) and held for an additional 2 min prior to adding 8 ul of Rnase H2 (120 mU) enzyme mixture. Each reaction (25 μL) was incubated at 65, 60, 55, 50, or 45 oC for 3 min or 6 min. 8 μL of sample was taken from each 25 μL reaction at time points of 5 and 20 min and quenched by 8 μL of loading dye. Digest reactions were resolved on a 20% of denature PAGE gel and each band intensity was quantified to evaluate the percentage of cleaved product (FIG. 24).

TABLE 1

Melting temperatures of duplexes modified with pruine analogues

```
5'-GAG TCT CGA CAH AGH TCC CAG AGG-3'      SEQ ID 1
3'-CTC AGA GCT GTC TCC AGG GTC TCC-5'      SEQ ID 2
Melting temperature 63° C.

5'-GAG TCT CGA CAH AGH TCC CAG AGG-3'      SEQ ID 1
3'-CTC AGA GCT GTT TCT AGG GTC TCC-5'      SEQ ID 3
Melting temperature 68° C.

5'-GAG TCT CGA CAH AGH TCC CAG AGG-3'      SEQ ID 1
3'-CTC AGA GCT GTG TCG AGG GTC TCC-5'      SEQ ID 4
Melting temperature 63° C.

5'-GAG TCT CGA CAH AGH TCC CAG AGG-3'      SEQ ID 1
3'-CTC AGA GCT GTA TCA AGG GTC TCC-5'      SEQ ID 5
Melting temperature 59° C.

5'-GAG TCT CGA CAK AGK TCC CAG AGG-3'      SEQ ID 6
3'-CTC AGA GCT GTC TCC AGG GTC TCC-5'      SEQ ID 2
Melting temperature 60° C.

5'-GAG TCT CGA CAK AGK TCC CAG AGG-3'      SEQ ID 6
3'-CTC AGA GCT GTT TCT AGG GTC TCC-5'      SEQ ID 3
Melting temperature 62° C.
```

TABLE 1-continued

Melting temperatures of duplexes modified with pruine analogues

```
5'-GAG TCT CGA CAK AGK TCC CAG AGG-3'    SEQ ID 6
3'-CTC AGA GCT GTG TCG AGG GTC TCC-5'    SEQ IS 4
Melting temperature 57° C.

5'-GAG TCT CGA CAK AGK TCC CAG AGG-3'    SEQ ID 6
3'-CTC AGA GCT GTA TCA AGG GTC TCC-5'    SEQ ID 5
Melting temperature 58° C.

5'-GAG TCT CGA CAI AGI TCC CAG AGG-3'    SEQ ID 7
3'-CTC AGA GCT GTC TCC AGG GTC TCC-5'    SEQ ID 2
Melting temperature 67° C.

5'-GAG TCT CGA CAI AGI TCC CAG AGG-3'    SEQ ID 7
3'-CTC AGA GCT GTT TCT AGG GTC TCC-5'    SEQ ID 3
Melting temperature 61° C.

5'-GAG TCT CGA CAI AGI TCC CAG AGG-3'    SEQ ID 7
3'-CTC AGA GCT GTG TCG AGG GTC TCC-5'    SEQ ID 4
Melting temperature 61° C.

5'-GAG TCT CGA CAI AGI TCC CAG AGG-3'    SEQ ID 7
3'-CTC AGA GCT GTA TCA AGG GTC TCC-5'    SEQ ID 5
Melting temperature 65° C.

5'-GAG TCT CGA CAG AGG TCC CAG AGG-3'    SEQ ID 8
3'-CTC AGA GCT GTC TCC AGG GTC TCC-5'    SEQ ID 2
Melting temperature 72° C.

5'-GAG TCT CGA CAG AGG TCC CAG AGG-3'    SEQ ID 8
3'-CTT AGA GCT GTT TCT AGG GTC TCC-5'    SEQ ID 3
Melting temperature 60° C.

5'-GAG TCT CGA CAA AGA TCC CAG AGG-3'    SEQ ID 9
3'-CTC AGA GCT GTC TCC AGG GTC TCC-5'    SEQ ID 2
Melting temperature 55° C.

5'-GAG TCT CGA CAA AGA TCC CAG AGG-3'    SEQ ID 9
3'-CTC AGA GCT GTT TCT AGG GTC TCC-5'    SEQ ID 3
Melting temperature 67° C.

5'-GAH TCT CGA CAG AGA TCC CAH AGG-3'    SEQ ID 10
3'-CTC AGA GCT GTC TCT AGG GTC TCC-5'    SEQ ID 11
Melting temperature 58° C.

5'-GAH TCT CGA CAG AGA TCC CAH AGG-3'    SEQ ID 10
3'-CTT AGA GCT GTT TCT AGG GTT TCC-5'    SEQ ID 12
Melting temperature 65° C.

5'-GAH TCT CGA CAG AGA TCC CAH AGG-3'    SEQ ID 10
3'-CTG AGA GCT GTG TCG AGG GTG TCC-5'    SEQ ID 13
Melting temperature 60° C.

5'-GAH TCT CGA CAG AGA TCC CAH AGG-3'    SEQ ID 10
3'-CTA AGA GCT GTA TCA AGG GTA TCC-3'    SEQ ID 14
Melting temperature 59° C.

5'-GAK TCT CGA CAG AGA TCC CAK AGG-3'    SEQ ID 15
3'-CTC AGA GCT GTC TCC AGG GTC TCC-5'    SEQ ID 2
Melting temperature 60° C.

5'-GAK TCT CGA CAG AGA TCC CAK AGG-3'    SEQ ID 15
3'-CTT AGA GCT GTT TCT AGG GTT TCC-5'    SEQ ID 12
Melting temperature 61° C.

5'-GAK TCT CGA CAG AGA TCC CAK AGG-3'    SEQ ID 15
3'-CTG AGA GCT GTG TCG AGG GTG TCC-5'    SEQ ID 13
Melting temperature 57° C.

5'-GAK TCT CGA CAG AGA TCC CAK AGG-3'    SEQ ID 15
3'-CTA AGA GCT GTA TCA AGG GTA TCC-5'    SEQ ID 14
Melting temperature 57° C.

5'-GAI TCT CGA CAG AGA TCC CAI AGG-3'    SEQ ID 16
3'-CTC AGA GCT GTC TCC AGG GTC TCC-5'    SEQ ID 2
Melting temperature 67° C.

5'-GAI TCT CGA CAG AGA TCC CAI AGG-3'    SEQ ID 16
3'-CTT AGA GCT GTT TCT AGG GTT TCC-5'    SEQ ID 12
Melting temperature 61° C.

5'-GAI TCT CGA CAG AGA TCC CAI AGG-3'    SEQ ID 16
3'-CTG AGA GCT GTG TCG AGG GTG TCC-5'    SEQ ID 13
Melting temperature 61° C.

5'-GAI TCT CGA CAG AGA TCC CAI AGG-3'    SEQ ID 16
3'-CTA AGA GCT GTA TCA AGG GTA TCC-5'    SEQ ID 14
Melting temperature 65° C.

5'-GAG TCT CGA CAG AGG TCC CAG AGG-3'    SEQ ID 8
3'-CTC AGA GCT GTC TCC AGG GTC TCC-5'    SEQ ID 2
Melting temperature 69° C.

5'-GAG TCT CGA CAG AGG TCC CAG AGG-3'    SEQ ID 8
3'-CTT AGA GCT GTT TCT AGG GTT TCC-5'    SEQ ID 12
Melting temperature 57° C.

5'-GAA TCT CGA CAA AGA TCC CAA AGG-3'    SEQ ID 17
3'-CTC AGA GCT GTC TCC AGG GTC TCC-5'    SEQ ID 2
Melting temperature 56° C.

5'-GAA TCT CGA CAA AGA TCC CAA AGG-3'    SEQ ID 17
3'-CTT AGA GCT GTT TCT AGG GTT TCC-5'    SEQ ID 12
Melting temperature 64° C.

5'-GAG TCT CGH CAG AGH TCC CAH AGG-3'    SEQ ID 18
3'-CTC AGA GCC GTC TCC AGG GTC TCC-5'    SEQ ID 19
Melting temperature 56° C.

5'-GAG TCT CGH CAG AGH TCC CAH AGG-3'    SEQ ID 18
3'-CTC AGA GCT GTC TCT AGG GTT TCC-5'    SEQ ID 20
Melting temperature 65° C.

5'-GAG TCT CGH CAG AGH TCC CAH AGG-3'    SEQ ID 18
3'-CTC AGA GCG GTC TCG AGG GTG TCC-5'    SEQ ID 21
Melting temperature 58° C.

5'-GAG TCT CGH CAG AGH TCC CAH AGG-3'    SEQ ID 18
3'-CTC AGA GCA GTC TCA AGG GTA TCC-5'    SEQ ID 22
Melting temperature 54° C.

5'-GAG TCT CGK CAG AGK TCC CAK AGG-3'    SEQ ID 23
3'-CTC AGA GCC GTC TCC AGG GTC TCC-5'    SEQ ID 19
Melting temperature 57° C.

5'-GAG TCT CGK CAG AGK TCC CAK AGG-3'    SEQ ID 23
3'-CTC AGA GCT GTC TCT AGG GTT TCC-5'    SEQ ID 20
Melting temperature 59° C.

5'-GAG TCT CGK CAG AGK TCC CAK AGG-3'    SEQ ID 23
3'-CTC AGA GCG GTC TCG AGG GTG TCC-5'    SEQ ID 21
Melting temperature 48° C.

5'-GAG TCT CGK CAG AGK TCC CAK AGG-3'    SEQ ID 23
3'-CTC AGA GCA GTC TCA AGG GTA TCC-5'    SEQ ID 22
Melting temperature 53° C.

5'-GAG TCT CGI CAG AGI TCC CAI AGG-3'    SEQ ID 24
3'-CTC AGA GCC GTC TCC AGG GTC TCC-5'    SEQ ID 19
Melting temperature 66° C.

5'-CAG TCT CGI CAG AGI TCC CAI AGG-3'    SEQ ID 24
3'-CTC AGA GCT GTC TCT AGG GTT TCC-5'    SEQ ID 20
Melting temperature 57° C.

5'-GAG TCT CGI CAG AGI TCC CAI AGG-3'    SEQ ID 24
3'-CTC AGA GCG GTC TCG AGG GTG TCC-5'    SEQ ID 21
Melting temperature 57° C.

5'-GAG TCT CGI CAG AGI TCC CAI AGG-3'    SEQ ID 24
3'-CTC AGA GCA GTC TCA AGG GTA TCC-5'    SEQ ID 22
Melting temperature 64° C.
```

TABLE 1-continued

Melting temperatures of duplexes modified with pruine analogues

```
5'-GAG TCT CGG CAG AGG TCC CAG AGG-3'    SEQ ID 25
3'-CTC AGA GCC GTC TCC AGG GTC TCC-5'    SEQ ID 19
Melting temperature 71° C.

5'-GAG TCT CGG CAG AGG TCC CAG AGG-3'    SEQ ID 25
3'-CTC AGA GCT GTC TCT AGG GTT TCC-5'    SEQ ID 20
Melting temperature 55° C.

5'-GAG TCT CGA CAG AGA TCC CAA AGG-3'    SEQ ID 26
3'-CTC AGA GCC GTC TCC AGG GTC TCC-5'    SEQ ID 19
Melting temperature 51° C.

5'-GAG TCT CGA CAG AGA TCC CAA AGG-3'    SEQ ID 26
3'-CTC AGA GCT GTC TCT AGG GTT TCC-5'    SEQ ID 20
Melting temperature 67° C.
```

1 μM of equimolar of oligonucleotides were combined in buffer containing 100 mM of NaCl, 20 mM of sodium cacodylate (pH 7). The heating and cooling cycle was performed between 20° C. to 85° C. with 0.5° C./min gradient.

However, H in some $T_m$ studies behaved more like a "universal" base than a "biversal" base. Thus, $T_m$ values of duplexes with two or three H:G mismatches were similar to those with two or three H:C matches. The $T_m$ of the H:A mismatch was lower than the $T_m$ of H:C by only ~0.7° C. per pair. In summary, H:T (by 2.4° C. per pair)>H:G (by 0.6° C. per pair)>H:C (by 0.7° C. per pair)>H:A. Further, duplexes with two or three H:G mismatches were more stable than K:G mismatches (~2.7° C. per pair); and the H:A pair was more stable than K:A (~0.6° C. per pair). The thermal stabiLty of duplexes where H is paired with all natural bases was further compared to the stability of duplexes having inosine (I) at the corresponding sites. Overall, I:C matches has the same stability as H:T matches, duplexes containing two or three I:A pairs were more stable than H:A mismatches (~2.6° C. per pair), and the I:G pair was less stable than H:G (~0.6° C. per pair). In summary I:C>(by 1.1° C. per pair) >I:A (by 2° C. per pair)>I:T≈I:G.

Example 4

Primer Extension and PCR

Biversal H Support PCR

DNA containing H can prime on DNA/RNA templates. Results with K were consistent with results from Brown (26). Primers targeted the consensus segments of the reverse transcriptase gene of HIV-1 B. Biversal H's or K's replaced three or four As in primers at sites known to have high divergence. The wild-type sequence was taken from the consensus. The divergent target had transitio mutations of A to G and T to C in forward and reverse primer binding regions (Table 2).

TABLE 2

Primers and targets used in PCR

```
Standard primer forward
5'-TGG GAA GTT CAA TAA GGA ATA CCA CAT C-3'                          SEQ ID 27
Standard primer reverse
3'-GAC CTA CAT CCA CTA CGT ATA AAA AGT-5'                            SEQ ID 28

3H Primer forward
5'-TGG GAA GTT CAG TAA GGH ATA CCH CAT C-3'                          SEQ ID 29
3H Primer reverse
3'-GHC CTH CAT CCH CTA CGT ATA AAA AGT-5'                            SEQ ID 30

4H Primer forward
5'-TGG GAH GTT CAH TAA GGH ATA CCH CAT C-3'                          SEQ ID 31
4H Primer reverse
3'-GHC CTH CAT CCH CTA CGT ATH AAA AGT-5'                            SEQ ID 32

4K Primer forward
5'-TGG GAK GTT CAK TAA GGK ATA CCK CATC-3'                           SEQ ID 33
4K Primer reverse
3'-GKC CTK CAT CCK CTA CGT ATK AAA AGT-5'                            SEQ ID 34

4I Primer forward
5'-TGG GAU GTT CAI TAA GGI ATA CCI CAT C-3'                          SEQ ID 35
4I Primer reverse
3'-GIC CTI CAT CCI CTA CGT ATI AAA AGT-5'                            SEQ ID 36

WT-90 target
5'-TGG GAa GTT CAa TAA GGa ATA CCCa CAT CCC GCA GGG TTA AAA AAG AAA AAA   SEQ ID 37
TCA GTA ACA GTA CtG GAt GTA GGt GAT GCA TAt TTT TCA-3'

Div4-90 target
5'-TGG GAg GTT CAg TAA GGg ATA CCg CAT CCC GCA GGG TTA AAA AAG AAA AAA    SEQ ID 38
TCA GTA ACA GTA CcG GAc GTA GGc GAT GCA TAc TTT TCA-3'
```

Figure 6:
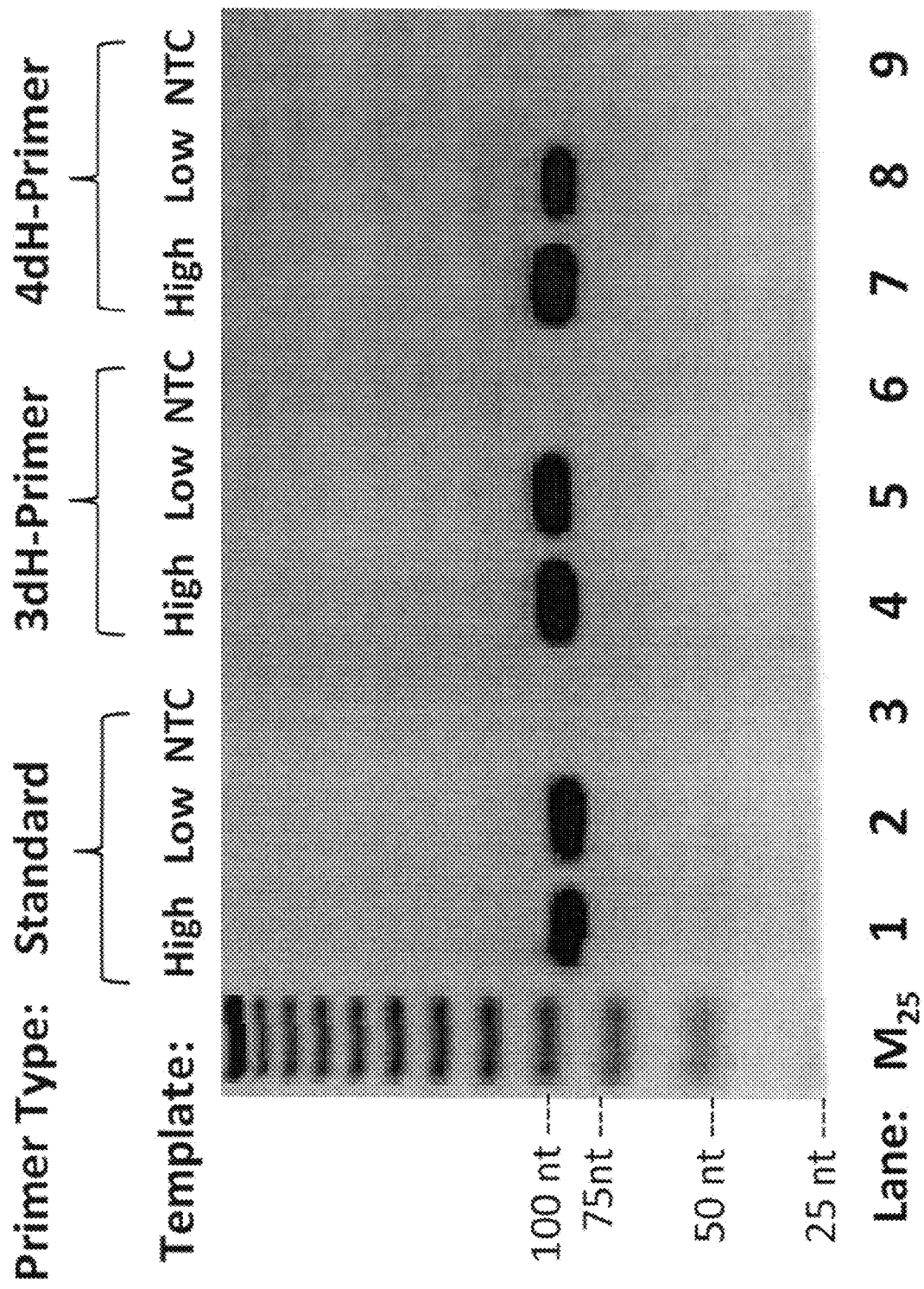
FIG. 6. PCR assays using standard primers or biversal analogous containing primers (3dH- and 4dH-primer). Lanes 1, 4, and 7: $3 \times 10^6$ copies of input target DNA. Lanes 2, 5, and 8: $3 \times 10^4$ copies of input target DNA. Lanes 3, 6, and 9: no target controls (NTC). Amplicons from PCR assays were resolved on agarose gel (2.5%) and stained with ethidium bromide. $M_{25}$ indicated 25 bp DNA ladder.

Amplicons from PCR (Taq) were resolved by agarose gel electrophoresis (FIG. 6). Both 3H- and the 4H-primer gave clean, full-length amplicons at rates similar to rates of amplicons generation with perfectly matched standard primers. This showed that H-containing primers efficiently hybridize with the wild-type targets, consistent with the biophysical studies. Further, these results show that Taq DNA polymerase can use biversal H-containing DNA as a template incorporating a standard dNTP opposite H to support the PCR (FIG. 6).

Figure 7:
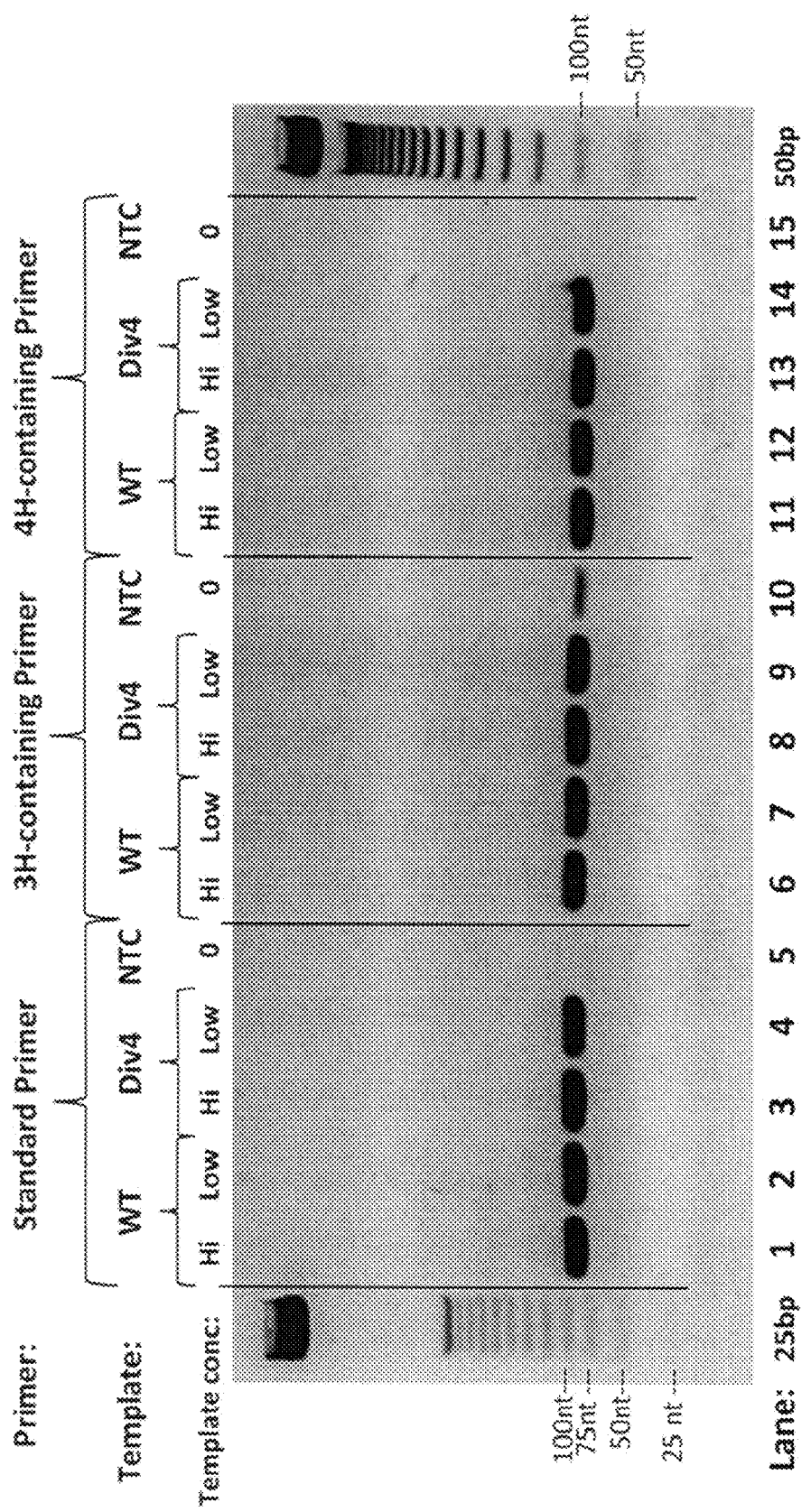
FIG. 7. PCR assays using standard primers or biversal 3H- and 4H-containing primers. Lanes 1, 6, and 11: $3 \times 10^6$ copies of wild type target (WT). Lanes 2, 7, and 12: $3 \times 10^4$ copies of wild type target (WT). Lanes 3, 8, and 13: $3 \times 10^6$ copies of divergent target (Div4). Lanes 4, 9, and 14: $3 \times 10^4$ copies of divergent target (Div4). Lanes 5, 10, and 15: no target controls (NTC). Amplicons from PCR assays were resolved on agarose gel (2.5%) and stained with ethidium bromide. 25 bp DNA ladder (left) and 50 bp DNA ladder (right).
Figure 8:
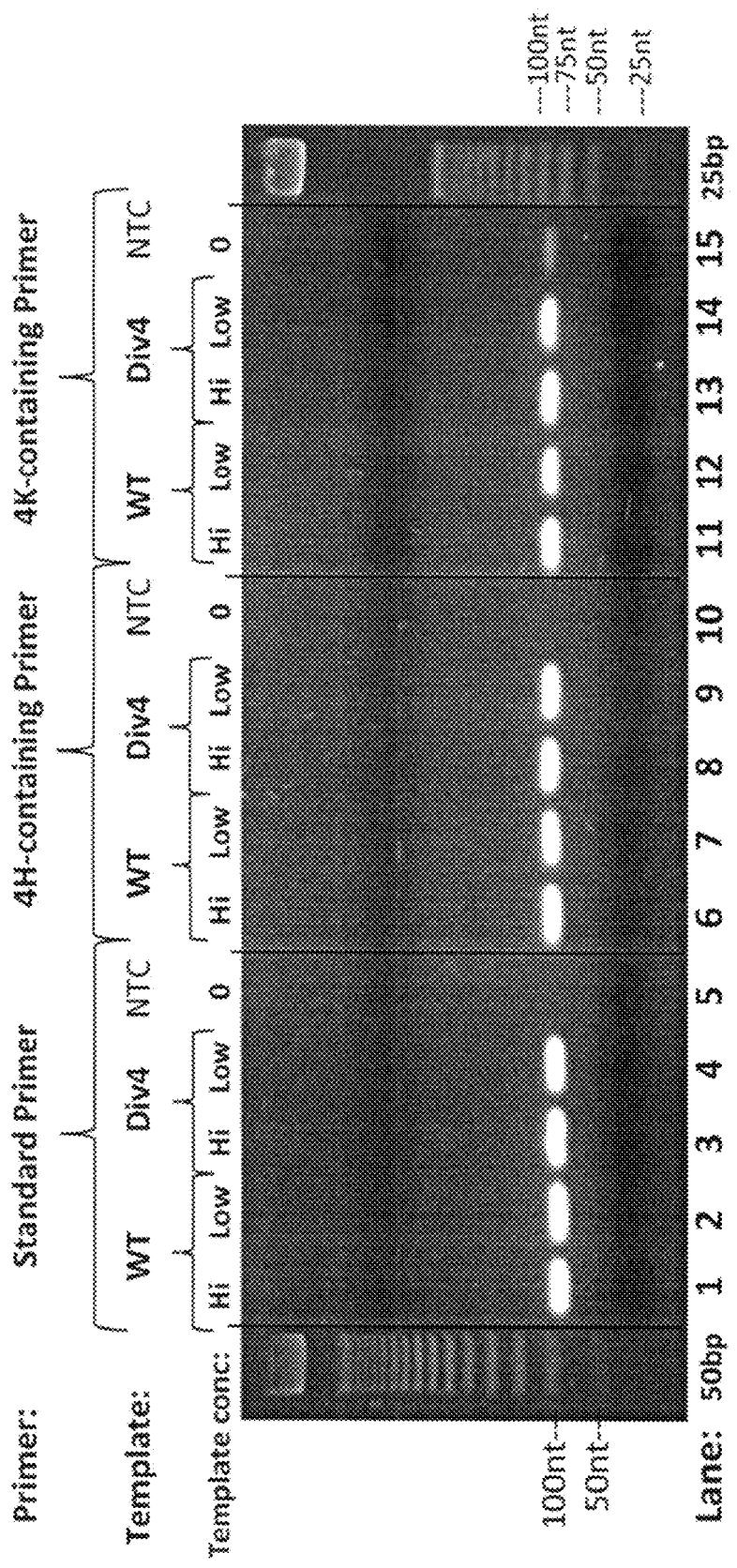
FIG. 8. Results of PCR assays using standard primers or biversal 4H- and 4K-containing primers. Lanes 1, 6, and 11: $3 \times 10^6$ copies of wild type target (WT). Lanes 2, 7, and 12: $3 \times 10^4$ copies of wild type target (WT). Lanes 3, 8, and 13: $3 \times 10^6$ copies of divergent target (Div4). Lanes 4, 9, and 14: $3 \times 10^4$ copies of divergent target (Div4). Lanes 5, 10, and 15: no target controls (NTC). 50 bp (left) and 25 bp (right) DNA ladder. Staining is with ethidium bromide.

PCR products from 3H- and 4H-primers were cloned and sequenced (SI Table S1). Results showed that biversal H directed incorporation of dTTP 95% of the time, and dCTP 5% of the time. In contrast, Brown's biversal K directed incorporation of dTTP 87% the time and dCTP 13% of the time.[32] The statistics are not large enough to draw conclusions about the influence of context on selectivity.
Manage Sequence Divergence in PCR Amplification To evaluate the ability of biversal-containing primers to amplify targets with mutations, a target that had diverged at four sites, replacing A's by G's in one and T's by C's in another, was probed in two concentrations ("Hi"=$3\times10^6$ copies; "Lo"=$3\times10^4$ copies); a consensus "wild type" target ($3\times10^6$ or $3\times10^4$ copies of Wt-90) was added to a PCR reaction mixture. Standard primers with four A:C mismatches were used to illustrate the value of the biversal (Table 2), all with three replicates. Amplicons were resolved by electrophoresis (FIG. 7 and FIG. 8).

Figure 9:
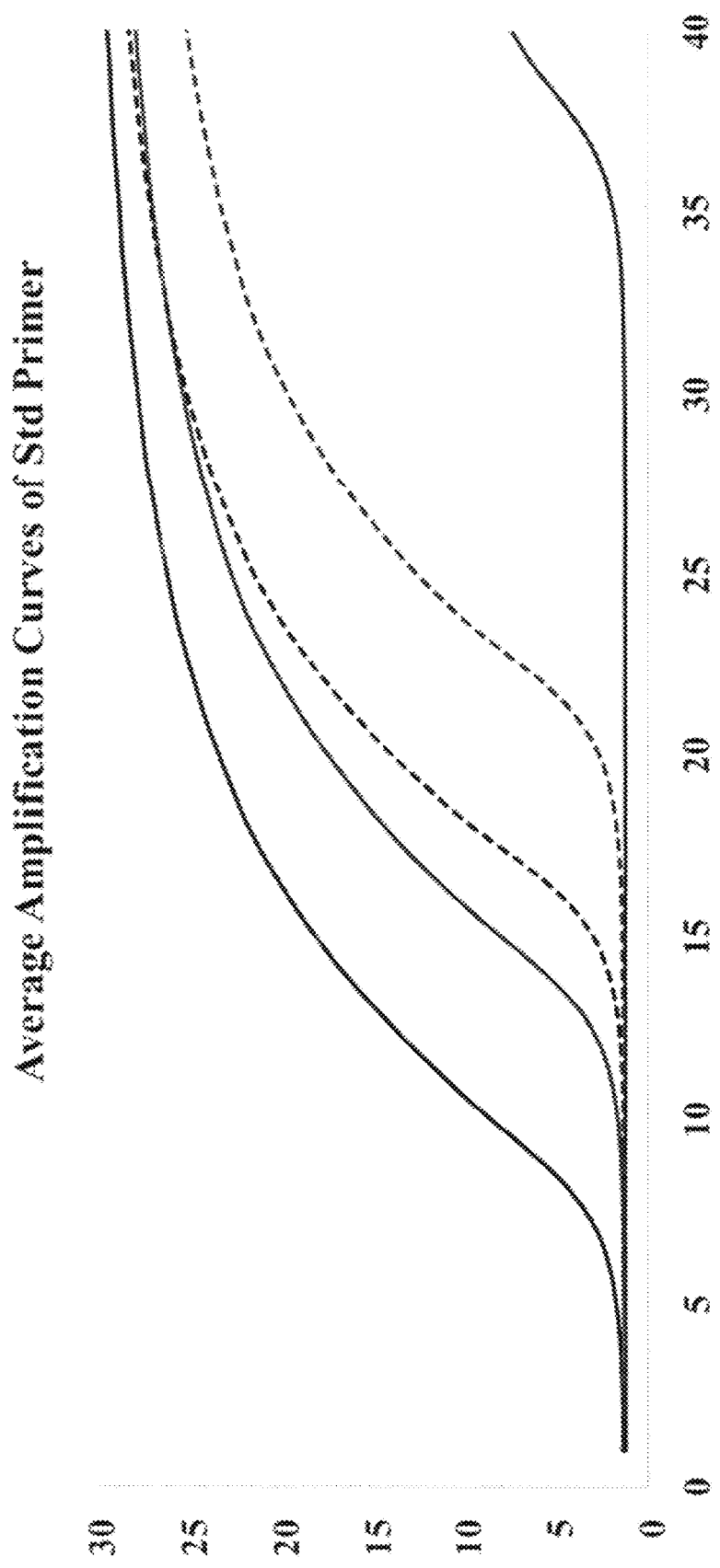
FIG. 9. Real-time PCR curves show the amplification of standard primer on wild type (WT) or divergent (Div4) consensus targets. Amplification was monitored by the fluorescence of EvaGreen® dye at two target concentrations, $3 \times 10^6$ copies (Hi) or $3 \times 10^4$ copies (Lo) per assay. NTC indicate no template control. All curves represent three replicates. From top to bottom, curves show targeting on WT-Hi (Solid), Div4-Hi (Solid), WT-Lo (dashed), Div4-Lo (dashed), and no-template control.

For standard primers, signal threshold was passed after 6.7 cycles (FIG. 9 and FIG. 13); the target with four A:C mismatches required 12.1 cycles at high target concentrations (Div4-Hi). With target at lower concentrations, the mismatched primer was also less efficient. This showed clearly the value of biversality (FIG. 13).

Figure 10:
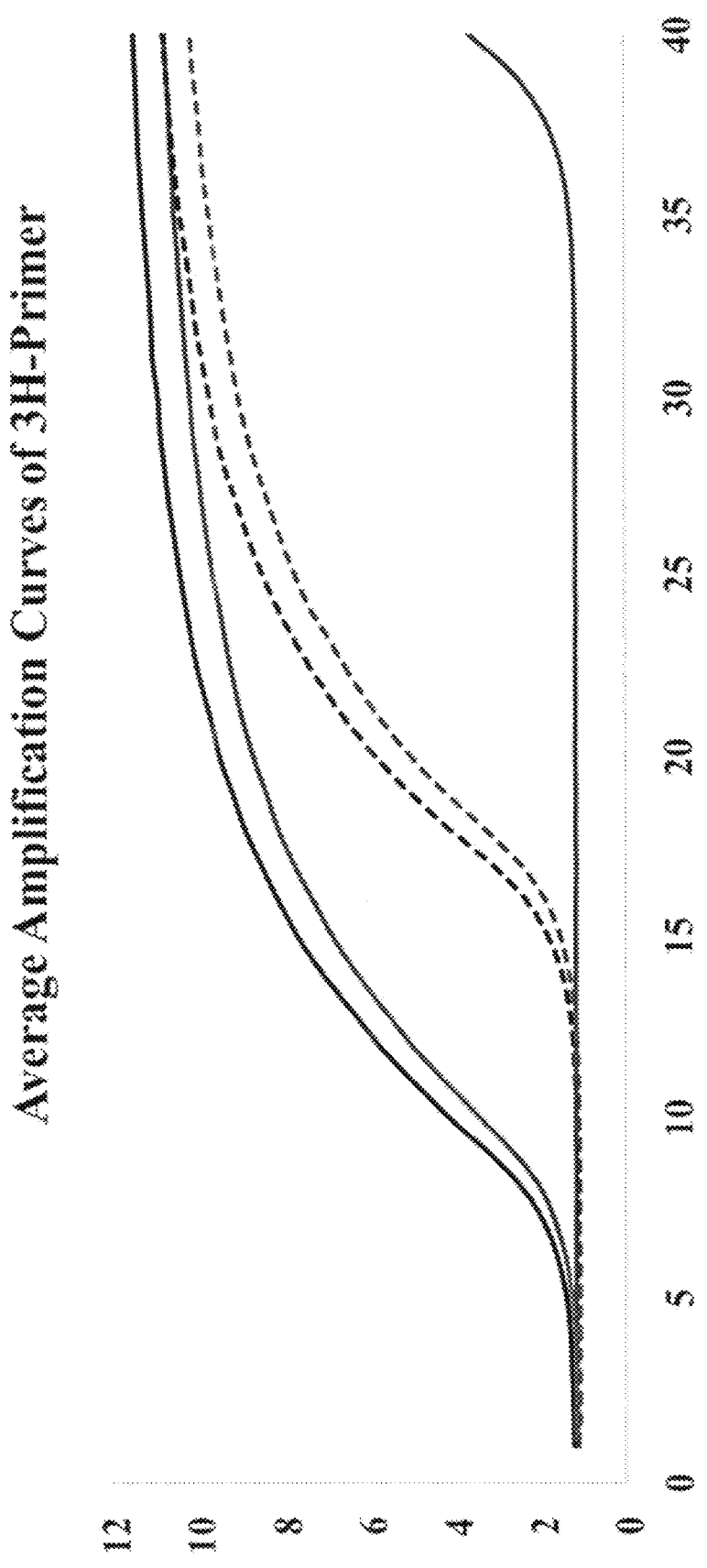
FIG. 10. Real-time PCR curves show the amplification of 3H-primer targeting on wild type (WT) or divergent (Div4) consensus targets. Amplification efficiency was monitored using the fluorescence of EvaGreen® dye at two target concentrations, $3 \times 10^6$ copies (Hi) or $3 \times 10^4$ copies (Lo) per assay, NTC indicates no template control. All curves represent three replicates. From top to bottom, curves show targeting on WT-Hi (solid), Div4-Hi (Solid), WT-Lo (dashed), Div4-Lo (dashed), and no-template control.
Figure 13:
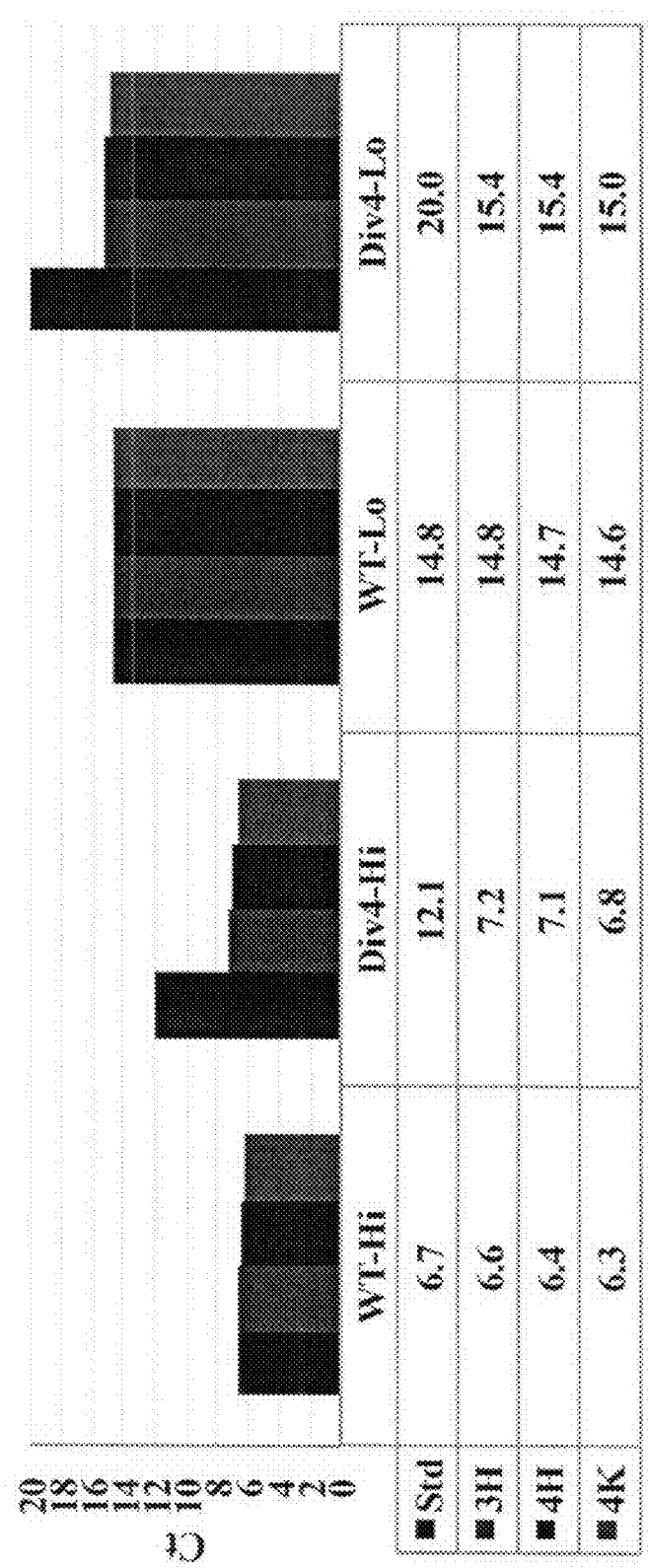
FIG. 13. Bar graph showing the PCR performance of purine biversai (3H, 4H, and 4K) primer; by Ct (the number of cycles to threshold). Within each cluster of four bars, shown ore (a) amplification of standard primer (Std) on wild type (WT) and divergent (Div4) targets at high (Hi) or low (Lo) target. (b): amplification of 3H-primer on WT and Div4 targets at both target concentrations. (c) performance of 4H-primers. (d) performance of 4K-primers. All primers were used at 1 µM final concentrations.
Figure 14:
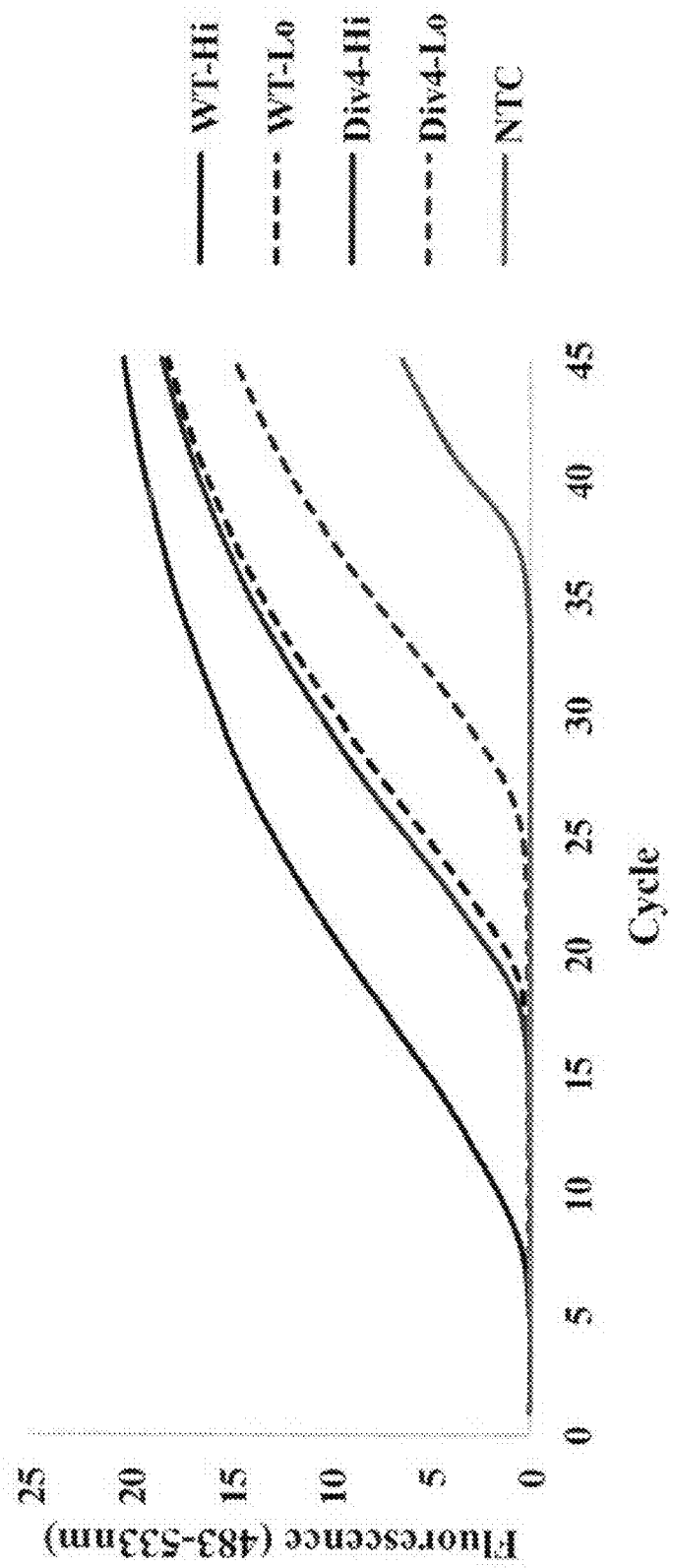
FIG. 14. Real-time PCR curves show the amplification of standard primer targeting on wild type consensus (WT) or divergent (Div4) targets. Amplification efficiency was monitored using the fluorescence of EvaGreen dye at two target concentrations, $3 \times 10^6$ copies (Hi) or $3 \times 10^4$ copies (Lo) per assay. NTC indicates no template control. All curves represent three replicates.

With both H and K at high and low target concentrations, amplification effiicierteleS were, essentially identical (FIG. 10 and FIG. 13). Paralleling the higher affinity of K for T over C, the Ct values were 6.3 and 6.8 at high target concentrations, and 14.6 and 15.0 at low target concentrations (4K). The ΔCt here is 0.4-0.5. Interestingly, the greater preference of H for T versus C was not manifested in the amplification efficiencies. The Ct values were 6.6 and 7.2 at high target with three H's, and 6.4 and 7.1 with four H's. The corresponding numbers at low target with three H's were 14.8 and 15.4, versus 14.7 and 15.4 with four H's (3H and 4H) (FIG. 13).

Fluorescence of EvaGreen bound to products from H- and K-containing primers is 30-50% of that from standard primers (FIGS. 9-12). However the PCR amplicons from each assay showed almost the same intensity by agarose gel/ethidium bromide analysis (FIGS. 7 and 8). This suggests that EvaGreen intercalates less well in a duplex containing biversals, is intrinsically less fluorescent upon binding, or has its fluorescence quenched.

Figure 11:
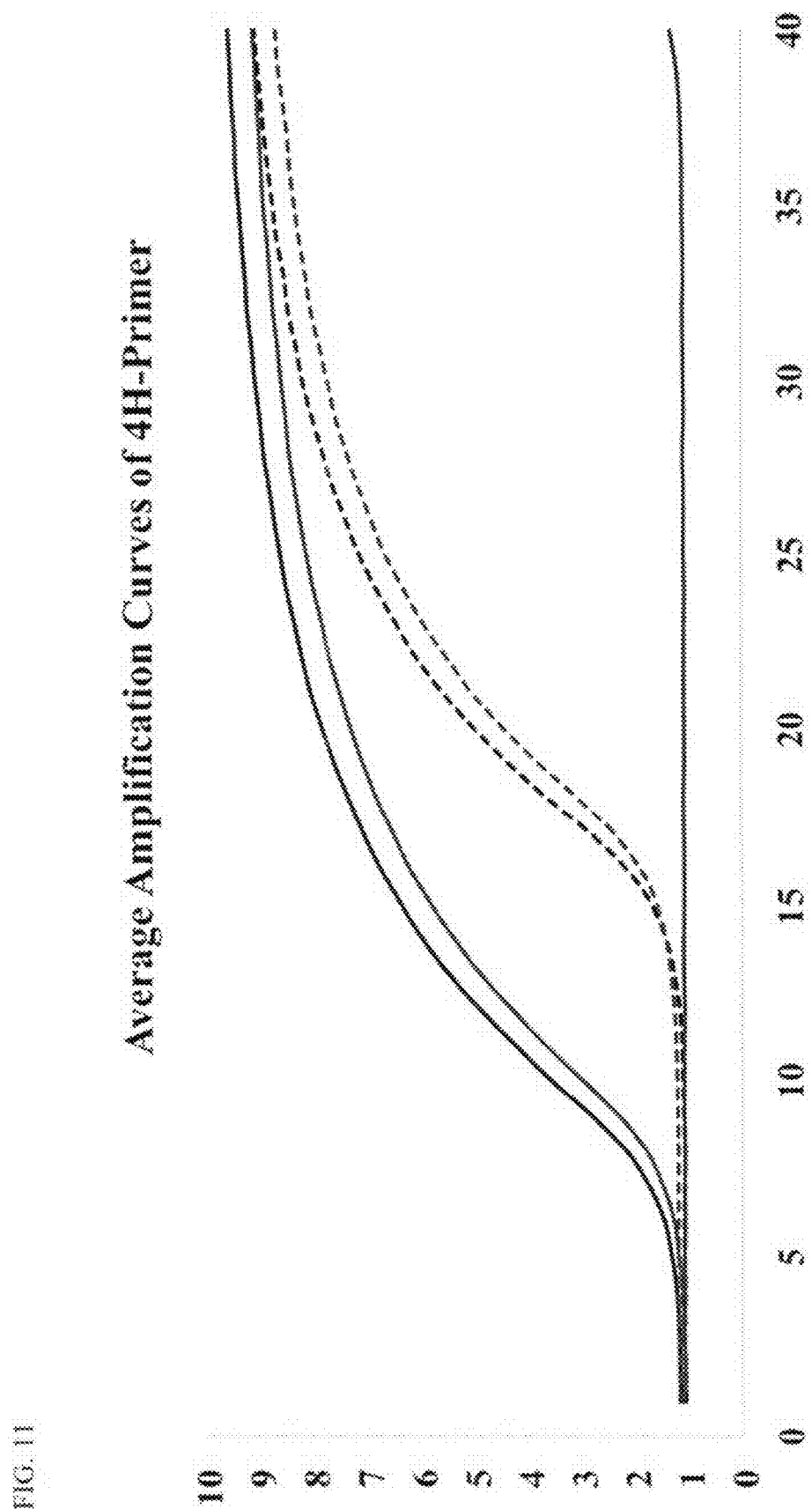
FIG. 11. Real-time PCR curves show the amplification of 4H- primer targeting on wild type (WT) or divergent (Div4) consensus targets, Amplification efficiency was monitored by measuring the fluorescence of EvaGreen® dye at two target concentrations, $3 \times 10^6$ copies (Hi) or $3 \times 10^4$ copies (Lo) per assay. NTC indicates no template control. All curves represent three replicates. From top to bottom, curves show targeting on WT-Hi (solid), Div4-Hi (Solid). WT-Lo (dashed), Div4-Lo (dashed), and no-template control.
Figure 12:
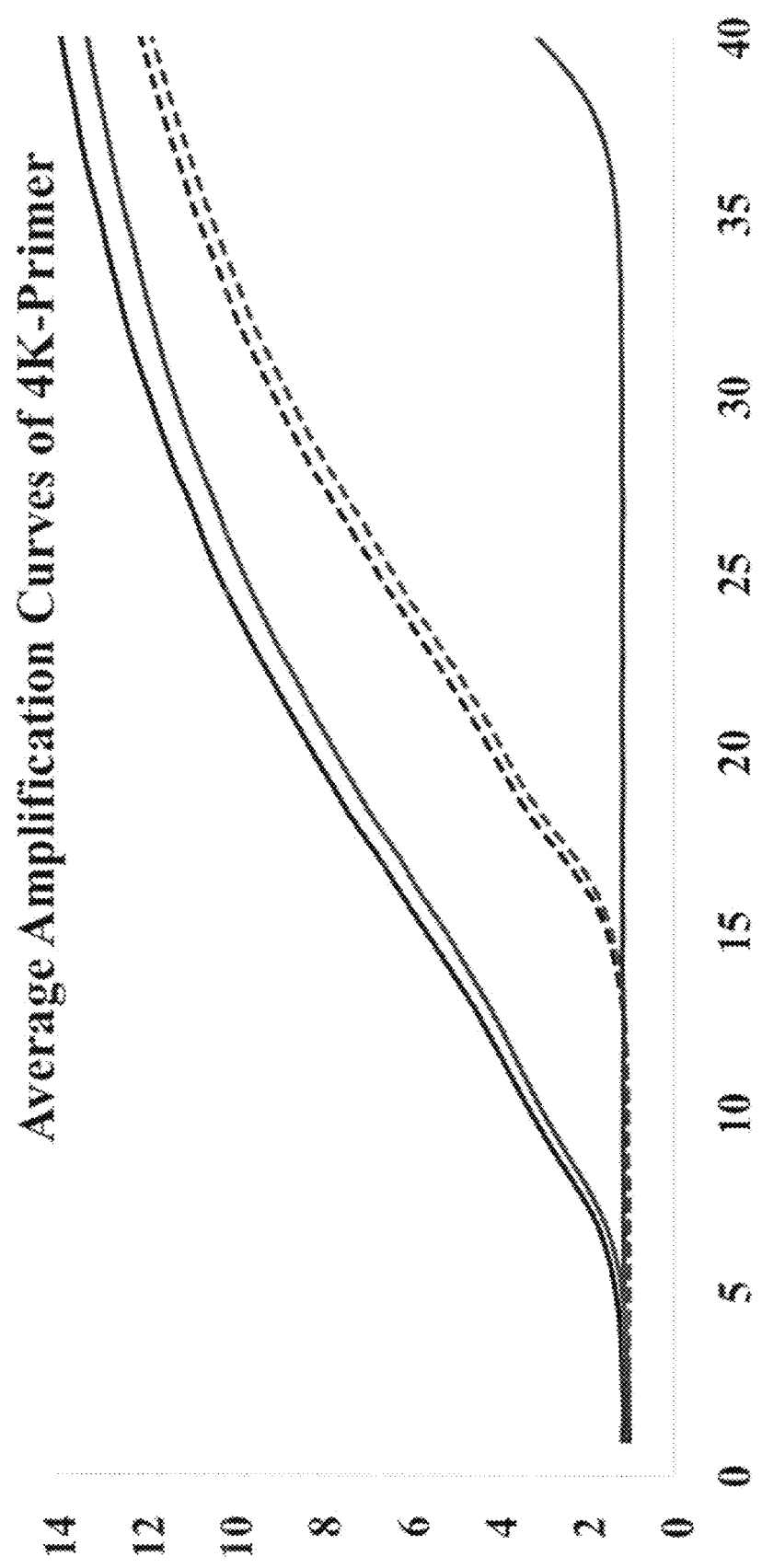
FIG. 12. Real-time PCR curves show the amplification of the 4K-primer targeting on wild type (WT) or divergent (Div4) consensus targets. Amplification efficiency was monitorei meas wing the fluorescence of EvaGreen® dye at two target concentrations, $3 \times 10^6$ copies (Hi) or $3 \times 10^4$ copies (Lo) per assay. NTC indicates no template control. All curves represent three rephcates. From top to bottom, curves show targeting on WT-Hi (solid), Div4-Hi (Solid), WT-Lo (dashed), Div4-Lo (dashed), and no-template control.

Amplification curves from K-containing printers shown abnormal shapes (FIG. 12). This might be due to incorporation of both dTTP and dCTP opposite K, producing amplicon mixtures with K variously paired with T or C. In contrast, since H directs incorporation of primarily dTTP, later amplifications with the H-containing primer may be better. This is consistent with amplification curves, more sigmoidal with H than K (FIGS. 10 and 11).

Primers containing H were next compared with primers containing inosine (I) relative to standard primers (FIG. 14 to FIG. 17). All PCR conditions were the same, except that primer concentrations were reduced to 0.5 μM, and polymerase cone entranons were reduced to 0.05 unit/μL. Further, uracil-DNA glycosylase (UDG, NEB) and a mixture of dUTP/dTTP were added into PCR to prevent carry-over contamination.

Figure 16:
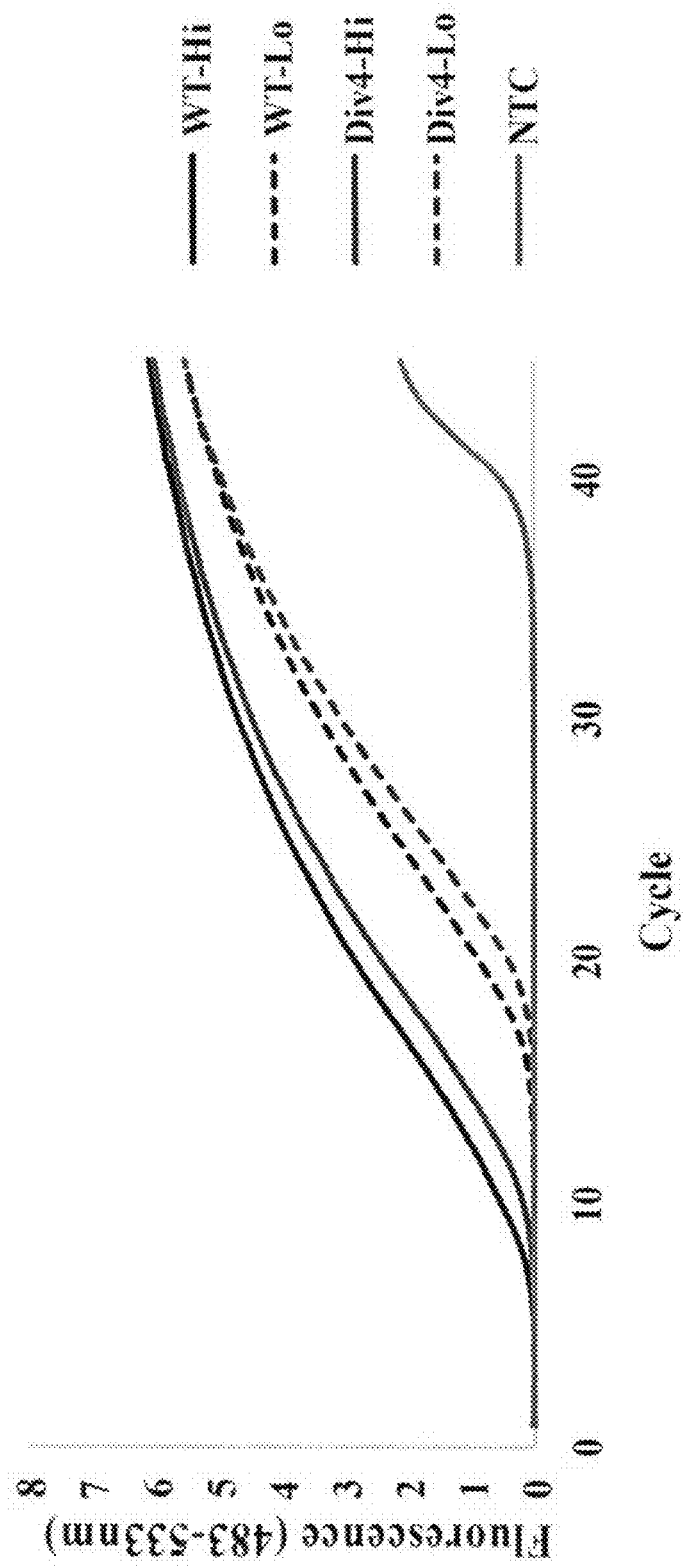
FIG. 16. Real-time PCR curves show the amplification of 4H-containing primers targeting on wild type consensus (WT) or divergent (Div4) targets. Amplification efficiency was monitored using the fluorescence of EvaGreen dye at two target concentrations, $3\times10^6$ copies (Hi) or $3\times10^4$ copies (Lo) per assay. NTC indicates no template control. All curves represent three replicates.
Figure 17:
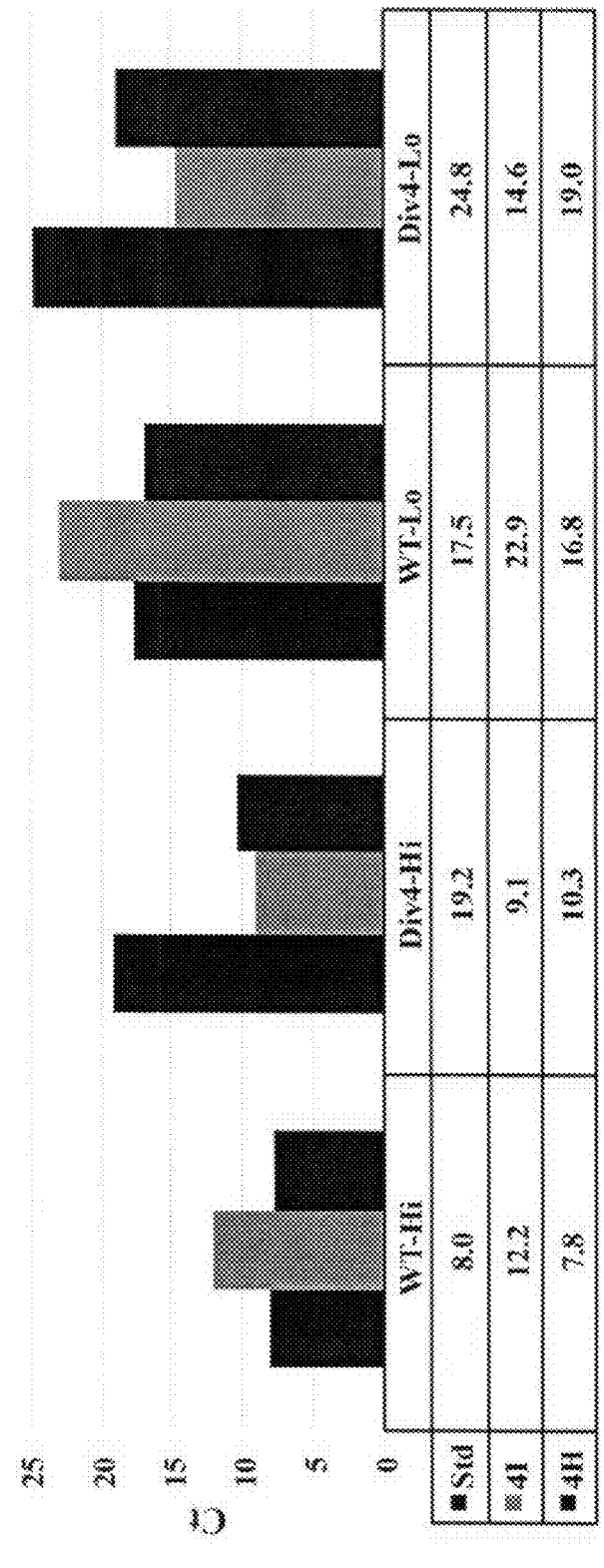
FIG. 17. Bar graph showing the PCR performance of purine analog (4I and 4H) primers by Ct. Left bars in each cluster: Standard primer (Std) on wild type (WT) and divergent (Div4) targets at higher (Hi) or lower (Lo) target concentration. Center bars in each cluster; The amplification of 4I-primer on WT and Div4 targets at Hi or Lo target concentration. Right bars in each cluster. The performance of 4H-primers. All primers were used at 0.5 µM final concentrations.

Amplification of all targets was slower reflecting lower primers and polymerase. For H-primers, CT values were 7.8 and 10.3 cycles for WT-Hi and Div4-Hi, respectively) (FIG. 16 and 17). Ct value was worse (16.8 and 19.0 cycle) for wild type and divergent targets (WT-Lo and Div4-Lo, FIG. 17). Delta-Ct, values were 2.5 and 2.2 for wild type and divergent targets at high and w concentrations (4H).

Figure 15:
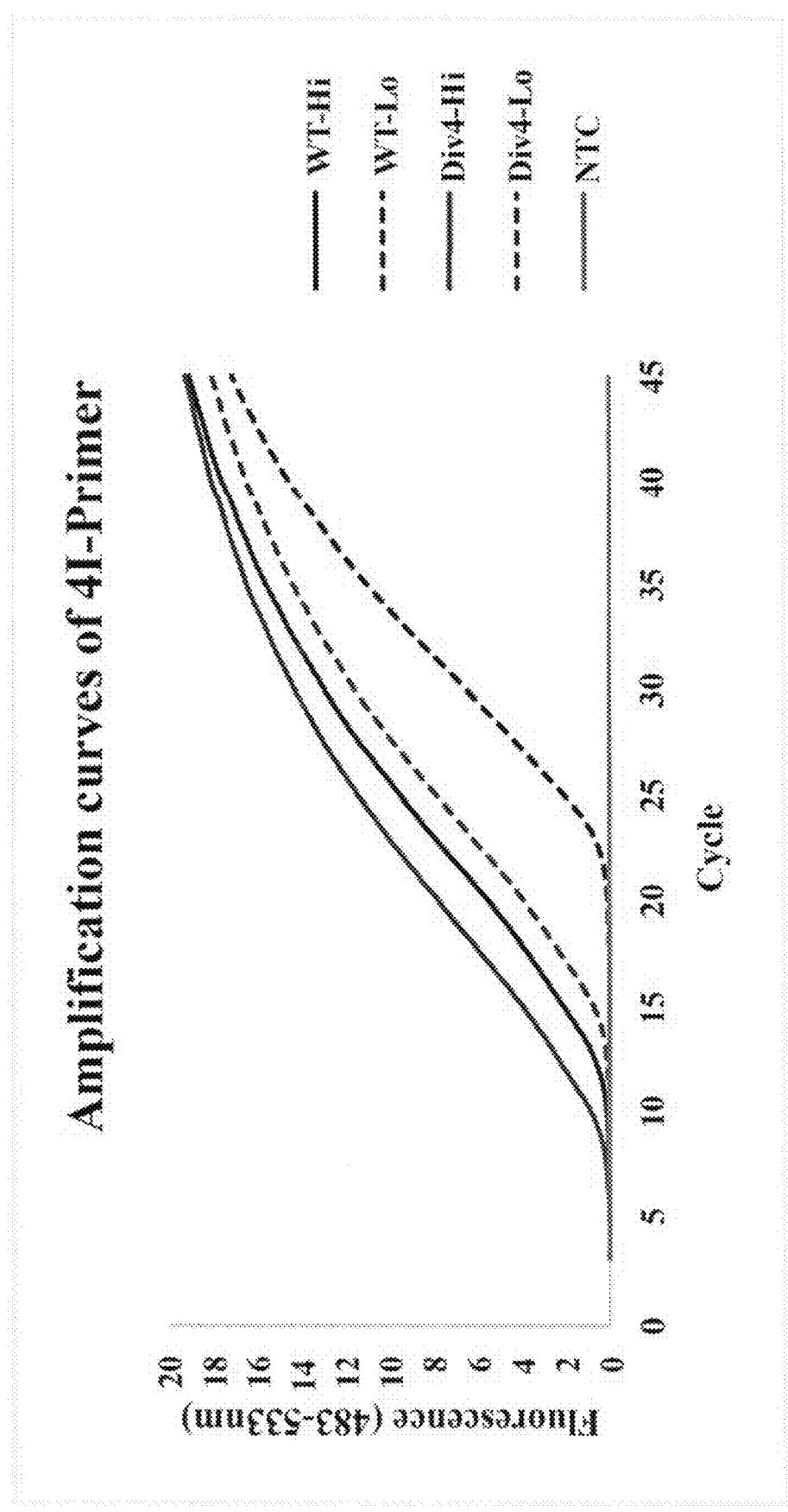
FIG. 15. Real-time PCR curves show the amplification of 4I-containing primers targeting on wild type consensus (WT) or divergent (Div4) targets. Amplification efficiency was monitored using the fluorescence of EvaGreen dye at two target concentrations, $3\times10^6$ copies (Hi) or $3\times10^4$ copies (Lo) per assay. NTC indicates no template control. All curves represent three replicates.

For I-primers, Ct values for the divergent target (I pairs C) were 9.1 and 14.6 at high and low target concentrations (FIGS. 15 and 17). However, Ct values for wild type target (I pairing with T) were 12.2 and 22.9 cycles, with delta-Ct values of 3.1 and 8.3 at high and low concentrations (4I). This correspond to the $T_m$ preference of I with T. For standard primers, delta-Ct between matched and mismatched targets were 11.2 and 7.3 cycles (FIG. 17). Overall, the H-containing primers had smaller delta-Ct differences between wild-type and divergent targets than standard and t-containing primers, showing an advantage of H (FIG. 14 to 17).

Figure 18:
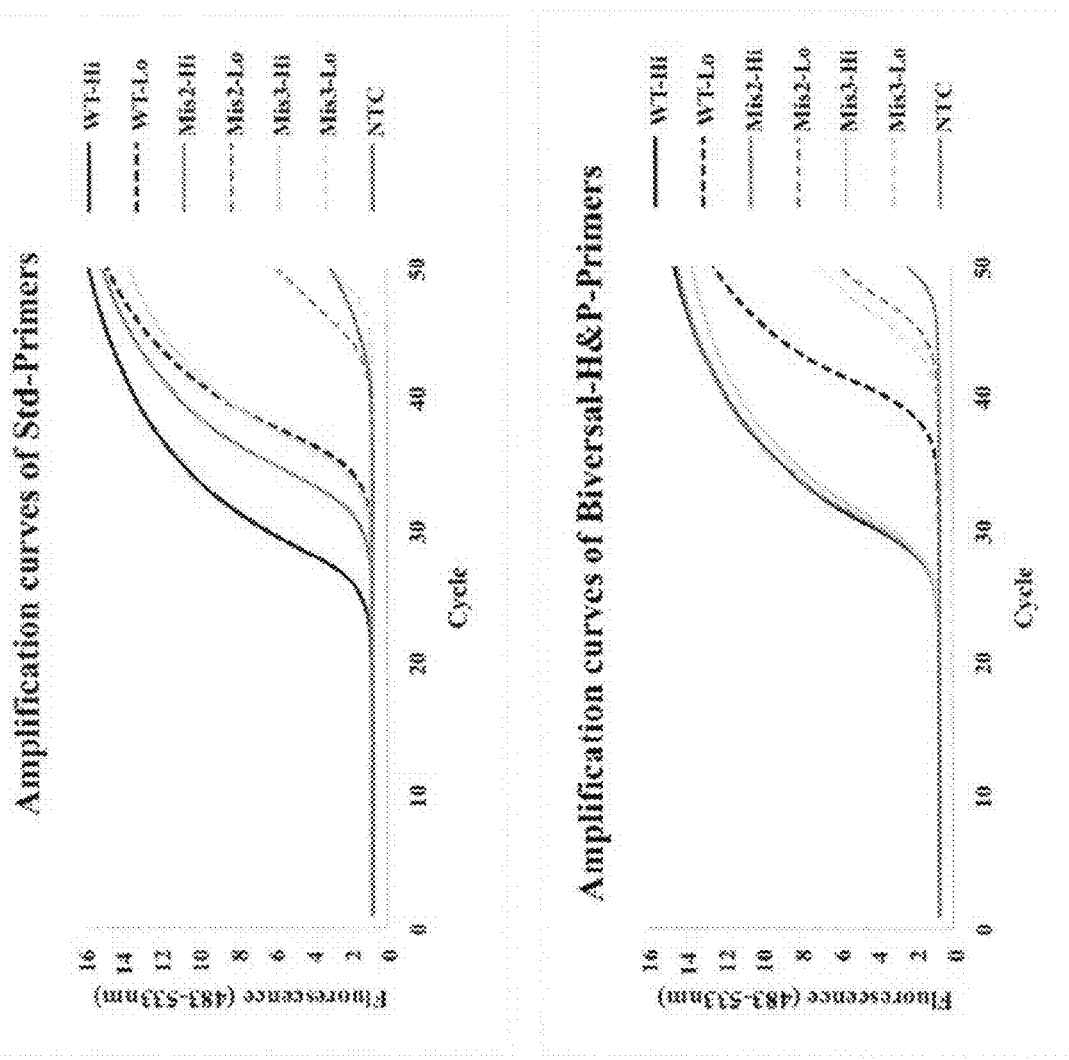
FIG. 18. Real-time PCR curves show the amplification of standard primers and primers containing both biversal H & P targeting on wild type (WT, HIV1-c consensus sequence) or divergent (Mis2 and Mis3 having four and six mutations, respectively) targets. Amplification efficiency was monitored based on the fluorescence of EvaGreen dye at two target concentrations, $1\times10^6$ copies (Hi) or $1\times10^4$ copies (Lo) per assay. NTC indicates no template control. All curves represent three replicates.

To test the combination of biversal H and P in primers to manage sequence divergence, standard primers, H- and P-primers were tested to amplify wild type (HIV-1C consensus) and divergent targets (four or six mutations in primer binding segments). As expected, H- and P-containing primers can amplify all targets and provide more uniform amplification than the standard primers (FIG. 18).

In addition, $T_m$s of amplicons from 1 μM of Std-, 3H, 4H-, and 4K-containing primers were 79.2, 79.4, 79.6, and 75.0° C. $T_m$s of the amplicons from 0.5 μM of Std-, 4H-, and 4I-containing primers and dUTP/dTTP mixture were 78.4, 78.6, and 73.3° C. The $T_m$s of amplicons from standard primers and H-primers were almost identical, and higher than amplicons from I- and K-containing primers, $T_m$s of these purine analog-containing amplicons also agreed with the melting temperature studies in Table 1.

Example 5

Ligation

Managing Sequence Divergence in Ligation SNP Analysis

The biversal-containing probes worked in ligation assays to detect medically significant SNPs with mutations nearby. This is especially a problem when seeking drug resistance in rapidly evolving RNA viruses. For example, the SNP in HIV reverse transcriptase that confers resistants to common drugs lies between sites that rapidly diverge in the coding region. These uninteresting SNPs confound efforts to detect the relevant SNPs in standard architectures that use standard nucleobases.

Ligation probes were designed with different numbers of H and K biversals (Table 3). Wild type target (Wt-g) was chosen from the consensus sequence of the RI gene of HIV-1 B; the divergent targets (Div2 and Div3) have either two or three mutations near the ligation site. Here, the medically irrelevant SNPs replaced C by T.

TABLE 3

Ligation probes with biversal purine

| | |
|---|---|
| Standard Probe donor | |
| 3'-CTT TTA ATC ATC TAA AGT CT-5' | SEQ ID 39 |
| Standard Probe acceptor | |
| 3'-CTT GAA TTA TTC TCT TGA GTT CTG AAG ACC CT-5' | SEQ ID 40 |

TABLE 3-continued

Ligation probes with biversal purine

| | |
|---|---|
| K-Probe donor with two K's<br>3'-CTT TTA ATC ATC TKA AKT CT-5' | SEQ ID 41 |
| K-Probe acceptor<br>3'-CTT KAA TTK TTC TCT TKA GTT CTG AAG ACC CT-5' | SEQ ID 42 |
| K-Probe donor with four K's<br>3'-CTT TTK ATC KTC TKA AKT CT-5' | SEQ ID 43 |
| H-Probe donor with two biversals<br>3'-CTT TTA ATC ATC THA AHT CT-5' | SEQ ID 44 |
| H-Probe acceptor<br>3'-CTT HAA TTH TTC TCT THA GTT CTG AAG ACC CT-5' | SEQ ID 45 |
| H-Probe donor with four biversals<br>3'-CTT TTH ATC HTC THA AHT CT-5' | SEQ ID 46 |
| I-Probe donor<br>3'-CTT TTI ATC ITC TIA AIT CT-5' | SEQ ID 47 |
| I-Probe acceptor<br>3'-CTT IAA TTI TTC TCT TIA GTT CTG AAG ACC CT-5' | SEQ ID 48 |
| Wt-g Target (underlined G is the SNP site)<br>5'-GAA AAT TAG TAG ATT TCA GA<u>G</u> AAC TTA ATA AGA GAA CTC AAG ACT TCT GGG A-3' | SEQ ID 49 |
| Div2 Target<br>5'-GAA AAT TAG TAG ACT TTA GA<u>G</u> AAT TTA ACA AGA GAA CTC AAG ACT TCT GGG A-3' | SEQ ID 50 |
| Div-Target<br>5'-GAA AAT TAG CAG ACT TTA GA<u>G</u> AAT TTA ACA AGA GAA TTC AAG ACT TCT GGG A-3' | SEQ ID 51 |

Figure 19:
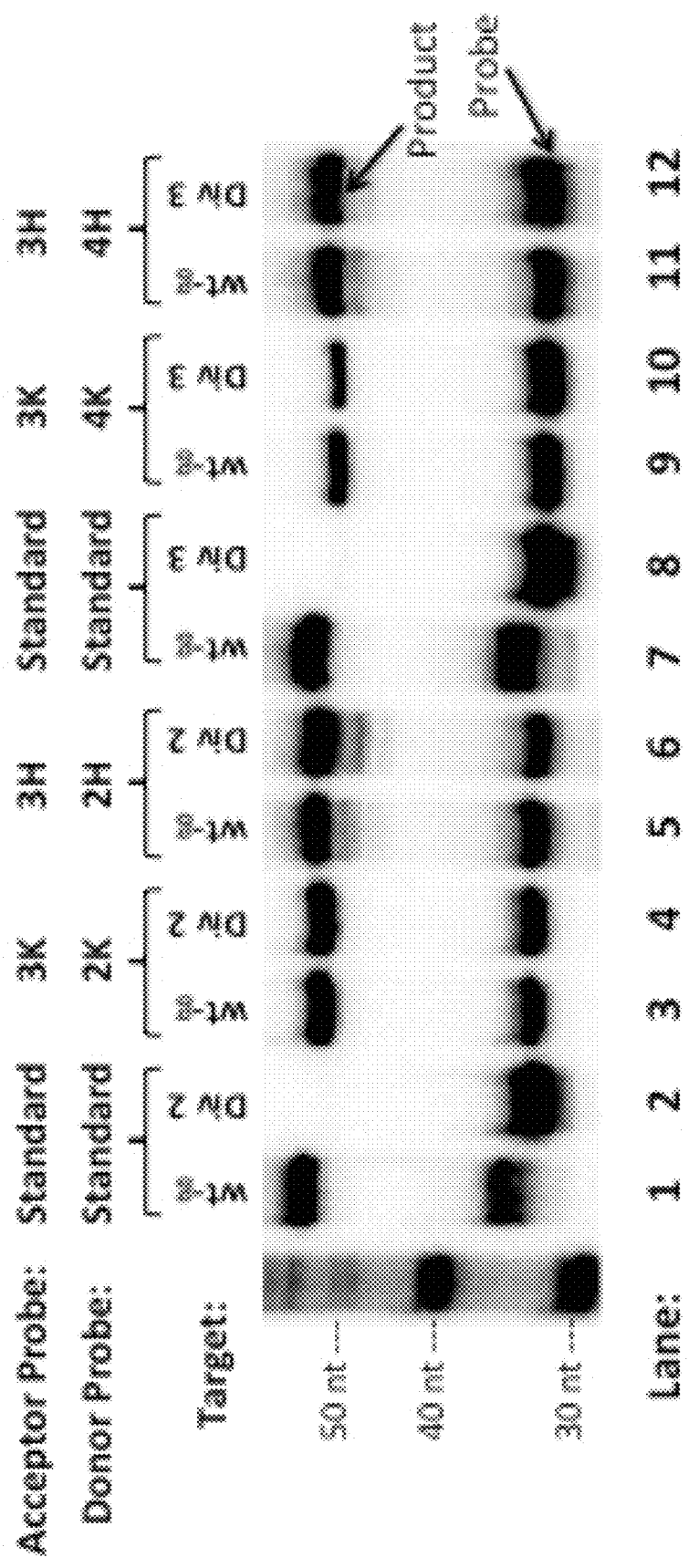
FIG. 19. Ligation of standard probes and purine analogue (K-, and H-containing) probes on wild type (Wt-g) or divergent (Div2 and Div3) targets. Acceptor probes were 5'-$^{32}$P labeled, ligation assays were resolved on PAGE gel (20% with 7 M urea). Lanes 1, 2, 7, and 8: Standard probes were ligated on wild type (wt-g) or divergent targets (Div2 and Div3). Lanes 3, 4, 9, and 10: Biversal K-probes were used. Lanes 5, 6, 11, and 12: Biversal H-probes were used.

Three H or K biversals were put in the acceptor probes, and two or four biversals were put in the donor probes, to pair with sites holding mutations in the targets. The efficiency of ligations were compared with standard probe ligations on wild type target (FIG. 19). As seen in FIG. 19 (lanes 1 and 7), standard probes gave ~50% ligation product with the perfect matched wild type target Iwt-g). In contrast, the same probes produced no ligation product at all with divergent targets (Div2 and Div3) that had two or three nearby medicalty irrelevant mismatches (FIG. 19, lane 2 and 8).

Here, biversality implemented via tautomerism has a large and potentially useful impact. For 2K-donor probes containing two K's to match medically irrelevant SNPs, ~50% ligation was seen for both targets wt-g and Div2. With the 4K-donor probe, ligation products decreased to ~30% for wild type target and further for the divergent:target (FIG. 19, lane 9 and 10). The decreased ligation may be caused by the lower $T_m$ of K:C and K:T pair relative to the A:T pair; alternatively, the freely rotating OMe group of biversal K may disturb double helix structure of the ligation probe and target, a disturbance recognized by the ligase enzyme. For H-containing probes, results were markedly better. Ligation products were produced for all targets at 50% levels. Further, the medically irrelevant mutations in the divergent targets had no significant impact on ligation efficiency for the 4H-containing probes (FIG. 19, lane 5, 6, 11, and 12).

Figure 20:
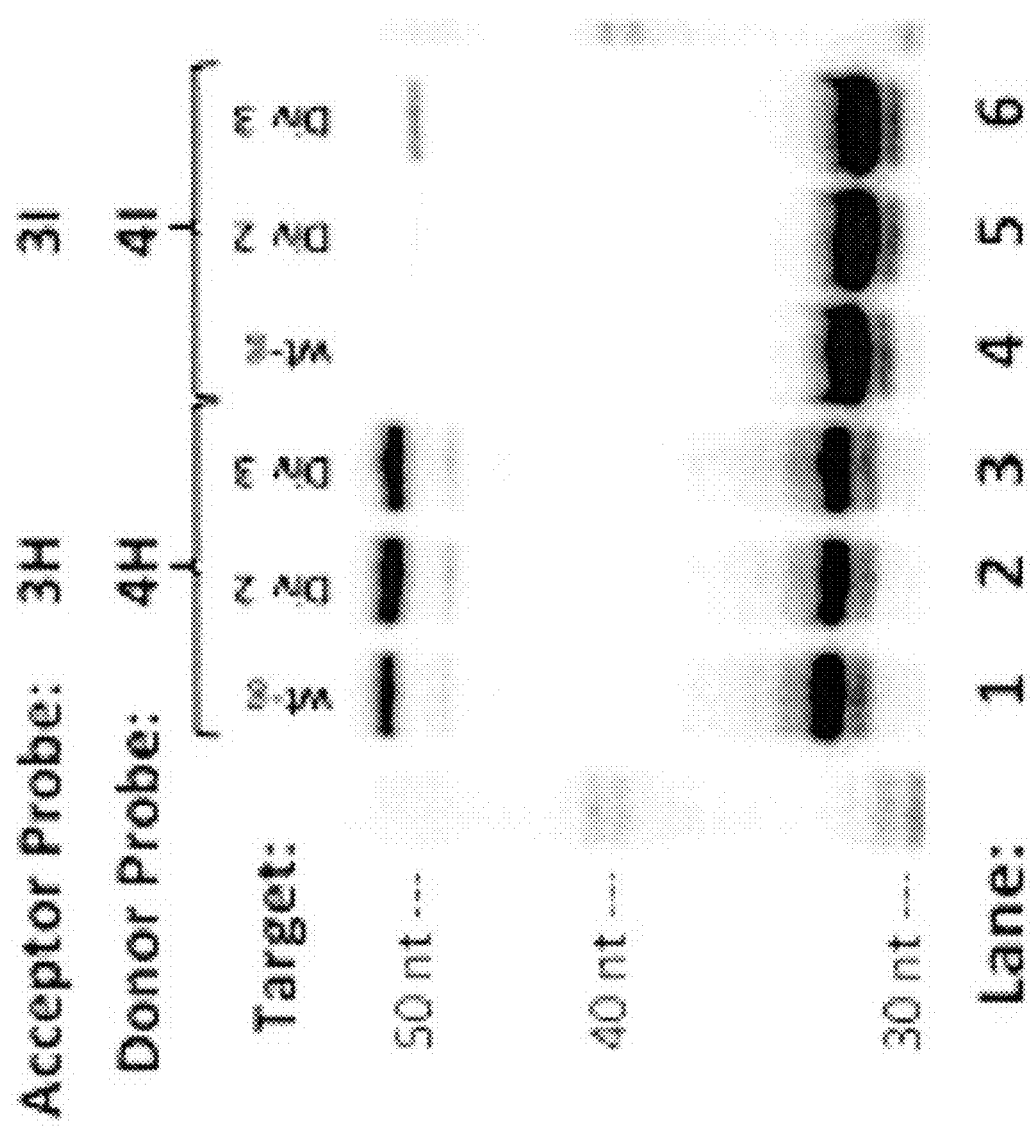
FIG. 20. Ligation of standard probes and purine analogue (H-, and I-containing) probes on wild type (Wt-g) or divergent (Div2 and Div3) targets. Acceptor probes were 5'-$^{32}$P labeled, ligation assays were resolved on PAGE gel (20% with 7 M urea). Lanes 1, 2, and 3: Biversal H-probes were ligated on wild type (wt-g) or divergent targets (Div2 and Div3). Lanes 4, 5, and 6: Biversal I-probes were used.

Next, H in the ligation probes was replaced with inosine (I). Inosine-containing probes failed to ligate on the wild-type (wt-g) and divergent (Div2) targets (FIG. 20, lane 4 and 5), and made negligible product on Div3 (FIG. 20, lane 6). In contrast, H-probes successfully produced products for all targets (FIG. 20, lane 1, 2, and 3). This shows another advantage of H over I.

Figure 21:
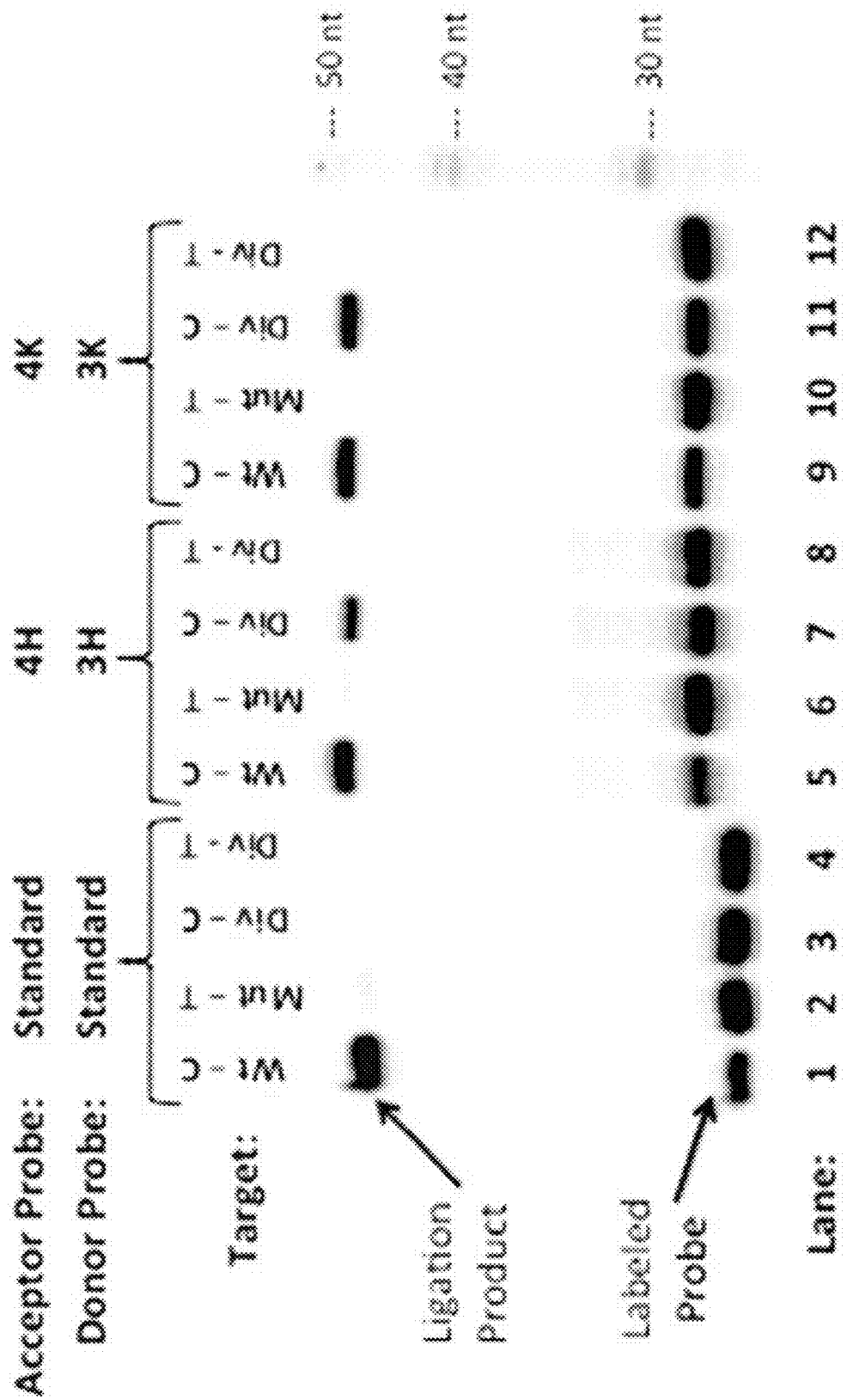
FIG. 21. SNP detection by ligation of standard and biversal H- and K- probes on wild type (Wt-C) or mutant (Mut-T, Div-C, Div-T) targets. Acceptor probes 5'-$^{32}$P labeled; products resolved on PAGE (20% with 7 M urea). Lanes 1, 2, 3, and 4: Ligation using standard probes on wild type or mutation targets. Lanes 5, 6, 7, and 8: with H-probes. Lanes 9, 10, 11, and 12: with K-probes. 10 bp DNA ladder (right).

To detect SNPs in variable targets in a ligation assay, standard probes can detect only perfectly matched targets (Table 3, Wt-C, FIG. 21, lane 1). As expected, standard probes generated no ligation products with targets having C to T mutations directly at the ligation sites (Mut-T, Div-T, FIG. 21, lane 2 and 4). However, they also failed with a matching at the exact ligation site if that site had flanking mismatches (Div-C) (FIG. 21, lane 3).

TABLE 4

Ligation probes with biversal purine for SNP detection

| | |
|---|---|
| Standard donor probe<br>3'-TCT TTT TTA GTC ATT GTC AT-5' | SEQ ID 52 |
| Standard acceptor probe<br>3'-GAC CTA CAT CCA CTA CGT ATA AAA AGT-5' | SEQ ID 28 |
| K-donor Probe<br>3'-TCT TTT TTA KTC ATT KTC KT-5' | SEQ ID 53 |
| K-acceptor Probe<br>3'-GKC CTK CAT CCK CTA CGT ATK AAA AGT-5' | SEQ ID 34 |
| H-donor Probe<br>3'-TCT TTT TTA HTC ATT HTC HT-5' | SEQ ID 54 |
| H-acceptor Probe<br>3'-GHC CTH CAT CCH CTA CGT ATH AAA AGT-5' | SEQ ID 32 |

TABLE 4-continued

Ligation probes with biversal purine for SNP detection

Wt-C Target
5'-AGA AAA AAT CAG TAA CAG TAC TGG ATG TAG GTG ATG CAT ATT TTT CA-3'    SEQ ID 55

Mut-T Target
5'-AGA AAA AAT CAG TAA CAG TAT TGG ATG TAG GTG ATG CAT ATT TTT CA-3'    SEQ ID 56

Div-C Target
5'-AGA AAA AAT TAG TAA CAG CAC CGG ATG TAG GCG ATG CAT ATT TTT CA-3'    SEQ ID 57

Div-T Target
5'-AGA AAA AAT TAG TAA CAG CAT CGG ATG TAG GCG ATG CAT ATT TTT CA-3'    SEQ ID 58

This failure was not seen with probes containing H and K. These not only ligate when held by perfectly matched targets (Wt-C, FIG. 21, lane 5 and 9), but also with mutations flanking that site (Div-C, FIG. 21, lane 7 and 11). H- and K-containing probes also differentiate a medically relevant C to T change at the ligation site, regardless of the presence of nearby medically irrelevant SNPs (Mut-T, Div-T, FIG. 21, lane 6, 8, 10 and 12).

Figure 22:
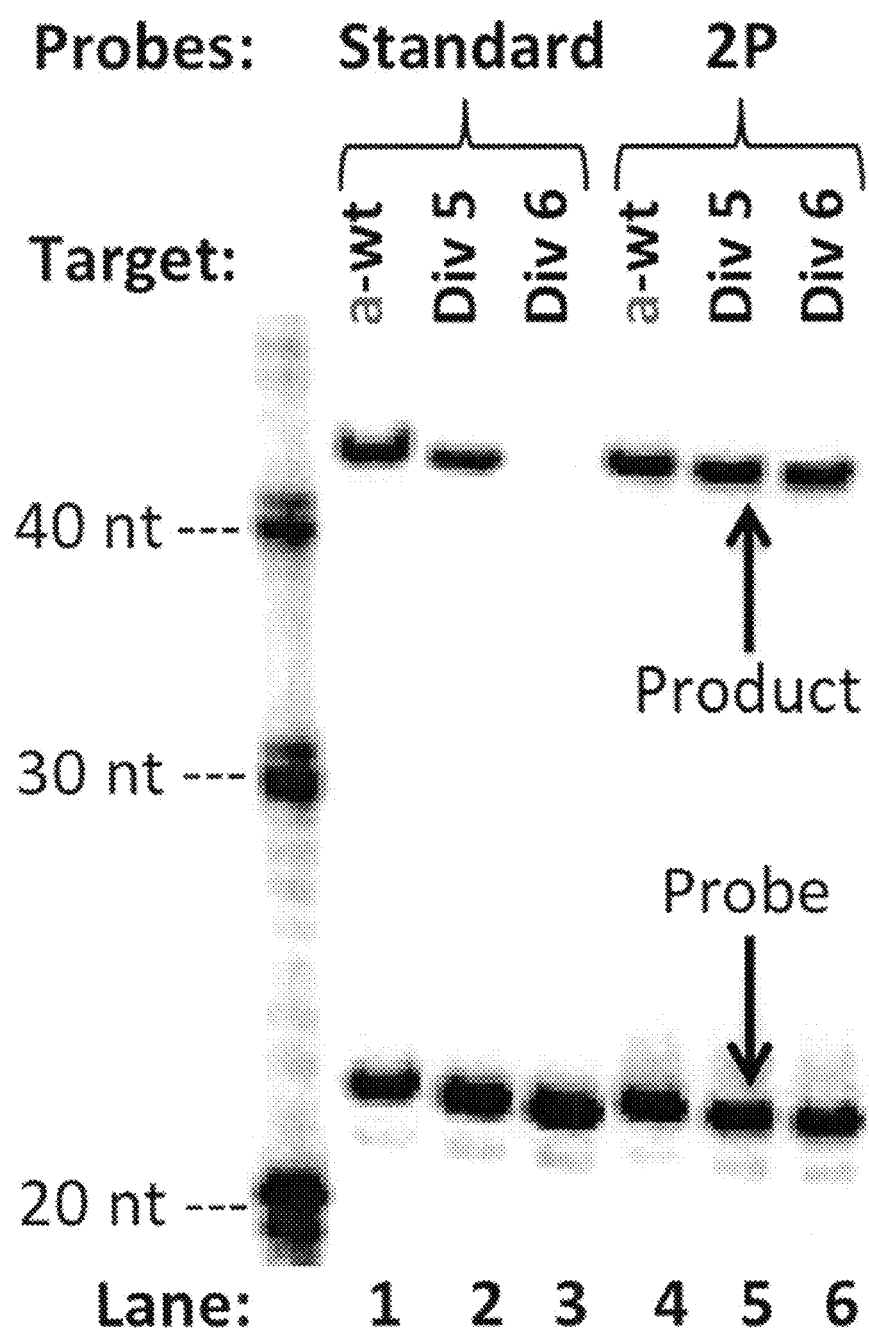
FIG. 22. Comparing the ligation efficiency of standard probes with biversal P-containing probes.
Figure 23:
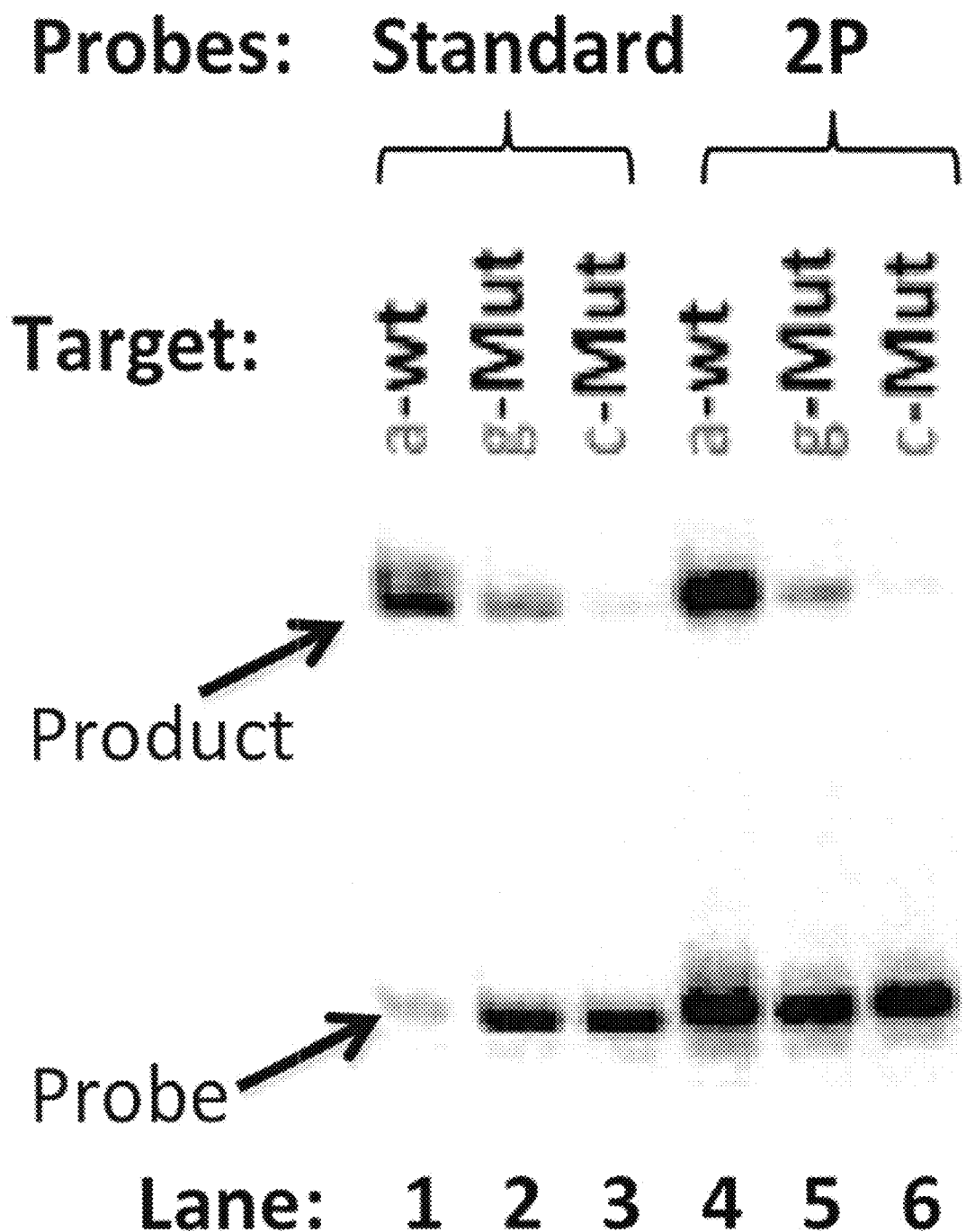
FIG. 23. Comparing the SNP detection of standard probes with biversal P-containing probes.

The biversal pyrimidine can also allow medically relevant SNPs to be detected amid medically irrelevant SNPs using ligation probes with P at the positions where A←→G transition mutations were found. P-containing probes generated equal amount of product for all targets (a-Wt, Div5 and Div6) (FIG. 22). This shows, as with K and H, that P-containing probes accommodate one or two mutations in regions flanking an interesting site. Standard probes failed to give ligation product if two mismatches (T:G) were present in the flanking region with two A to G mutations. Likewise, probes where I replaces P also failed to give products when two transition mutations (A to G) were in the flanking recon and caused two I:G mismatches (data not shown). For the SNP detection, biversal P-containing probes performed nearly identically as the standard probes to differentiate medically reievant SNP changes (FIG. 23).

General Protocol of Ligation Assay

Each ligation reaction mixture contained one $^{32}$P-labelled acceptor probe (final 100 nM), one donor probe (a $PO_4$ group at 5'-end of the donor probe, final 100 nM) and a target (final 100 nM) in 1× ligation reaction buffer. The substrate mixtures (15 µL) were first heated to 90° C. for 1 min in Bio-Rad Thermal Cycler with a heated lid, then cooled to the ligation reaction temperature (45° C. unless stated otherwise) at a speed of 0.2° C/s. The substrate inixtures (15 µL) were held at the action temperature until 5 µL of Taq DNA ligase (40 units per reaction) in 1× ligation buffer was added to give a final volume of 20 µL. The reaction mixtures (20 µL) were incubated at 45° C. for 5 min, 20 min, or 60 min. At the end ofthe incubation, 7 µL of reaction mixture was quenched by 7 µL of PAGE loading dye (containing 10 mM of EDTA and 95% of formamide), the ligation products and probes were resolved on a 20% denatured PAGE gel (7 M urea). (FIG. 29 to FIG. 23).

Comparing Amplification Efficiency of 3H-, 4H-, and 4K-Containing Primers: Real-Time PCR Wild type DNA templates ($3 \times 10^6$ and $3 \times 10^4$ copies of Wt-90) and divergent DNA templates ($3 \times 10^6$ and $3 \times 10^4$ copies of Div4-90) were amplified under 1× AmpliTaq Gold reaction buffer (15 mM Tris-HCl, 50 mM KCl, pH 8.3 at 25° C.), $MgCl_2$ (3 mM), dNTPs (each 0.2 mM), 2.5 units of Hot Start AmpliTaq Gold DNA polynterase (5 U/µL, ABI), and EvaGreen® dye (0.2 x, Biotium) in a 25 µL reaction mixture using four types of primers (somdard printer, 3H-containing primer, 4H-containing primer, or 4K-containing primer, Table 2) respectively. All PCRs and non-template control experiments (NTC) were performed under identical conditions for eaeh type of primer at 95° C. for 8 min, then, followed 40 cycles of (95° C. for 10 s, 50° C. for 30 s, 72° C. for 30 s) in the Roche LightCycler® 480 real-time PCR system. The LightCycler® 480 software calculates the threshold cycle (Ct) and the $T_m$ for each sample. Each assay was repeated twice. Upon the completion of the PCR, each sample (10 µL) was mixed with 6× agarose loading dye (2 µL, Promega), and analyzed on agarose gel (3%) electrophoresis.

Example 6

Biversals in Probe Cleavage

To detect a nucleotide at a medically relevant site (MRS), we used RNase H2 to cleave a probe only if the base at the MRS site matches the probe ribonucleotide (rC or rA). Such tests are confounded by variation at nearby medically irrelevant sites (MISs). In this example, three probes were used. The first contained only standard nucleotides (Std-probe) matching the MISs (standard probe). The second contained a "universal" nucleotide (inosine, 2I-probe) to match the MISs. The third used biversais (2K-probe) to match the MISs. The results are in FIG. 24.

DNA probes (embedded ribonucleotide, rC) with the MRS paired with G, "universal" nucleotide I, or the purine biversal K.

5'-CTC GTG AGG TGA TGrC AGG AGA TGG GAG GCG-3' rC-Std-Probe SEQ ID 59

5'-CTC GTG AGG TGI TGrC AIG AGA TGG GAG GCG-3' rC-2I-Probe SEQ ID 60

5'-CTC GTG AGG TGK TGrC AKG AGA TGG GAG GCG-3' rC-2K-Probe SEQ ID 61

These probe targets to give 3 clusters on left panel of FIG. 24. The 5 bars are ordered: 1) no-cleavage, 2) cleavage, 3) no cleavage, 4) cleavage, 5) no-cleavage. The rationale follows:

1) No target control. Expect no cleavage; no target-probe duplex exists for RNase H2 to cleave.

2) 3'-GAG CAC TCC ACT AcG TCC TCT ACC CTC CGC-5' SEQ ID 62

Target without change at the MRS (G); the matched MISs should be cleaved.

3) 3'-GAG CAC TCC ACT AcA TCC TCT ACC CTC CGC-5' SEQ ID 63

Target with G to A change at MRS, but still with matched MISs; RNase H2 cleaves non-specific.

4) 3'-GAG CAC TCC ACc AcGT tCT CTA CCC TCC GC-5'
SEQ ID 64
Target without change at the MRS (G), but mismatching at flanking MIS sites;
5) 3'-GAG CAC TCC ACc AcA TtC TCT ACC CTC CGC-5'
SEQ ID 65
Target with change at MRS (G to A) and mismatching at flanking MIS sites.
DNA probes (with embedded ribonucleotide, rA) with the MRS paired with T, "universal" nucleotide I, or the purine biversal K
5'-CTC GTG AGG TGA TGrA AGG AGA TGG GAG GCG-3' rA-Std-Probe SEQ ID 66
5'-CTC GTG AGG TGI TGrA AIG AGA TGG GAG GCG-3' rA-2I-Probe SEQ ID 67
5'-CTC GTG AGG TGK TGrA AKG AGA TGG GAG GCG-3' rA-2K-Probe SEQ ID 68 probe these targets to give 3 clusters on right panel, each of the 5 bars should be: 6) no-cleavage, 7) cleavage, 8) no-cleavage, 9) cleavage, 10) no-cleavage. 6) No target control: Expect no cleavage, as there is no target-probe duplex for RNase H2 to cleave.
3'-GAG CAC TCC ACT AcT TCC TCT ACC CTC CGC-5'
SEQ ID 69
Target without change at the MRS (T); matched MISs; expect cleavage with matched duplex.
3'-GAG CAC TCC ACT AcC TCC TCT ACC CTC CGC-5'
SEQ ID 70
Target with change at MRS (T to C), but matched MISs; RNase H2 has non-specific cleavage.
3'-GAG CAC TCC ACc AcT TtC TCT ACC CTC CGC-5'
SEQ ID 71
Target without change at the MRS (T), but mismatching at flanking MIS sites;
3'-GAG CAC TCC ACc AcC TtC TCT ACC CTC CGC-5'
SEQ ID 72
Target with change at MRS (T to C) and mismatching at flanking MIS sites.

REFERENCES

1. Korn, K., Weissbrich, B., Henke-Gendo, C., Heim, A., Jauer, C. M. Taylor, N. and Eberle, J. (2009) Single-point mutations cawing more than 100-fold underestimation of human immunodeficiency virus type 1 (HIV-1) load with the Cobas TaqMan HIV-1 real-time PCR assay, *J. Clin. Microbiol.*, 47, 1238-1240.
2. Drexler, J. F., de Souza Luna, L. K., Pedroso, C., Pedral-Sampaio, D. B., Queiroz, A. T., Brites, C., Netto, E. M. and Drosten, C. (2007) Rates of and reasons for failure of commercial human itranunodeficiency virus type 1 viral load assays in Brazil. *J. Clin. Microbiol.*, 45, 2061-2063.
3. Clutter, D. S., Rojas Sanchez, P., Rhee, S. Y. and Shafer, R. W. (2016) Genetic Variability of HIV-1 for Drug Resistance Assay Developments. *Viruses* 8, 48.
4. Glushakova, L. G., Bradley, A., Bradley, K. M., Alto, B. W., Hoshika, S., Hutter, D., Sharma, N., Yang, Z., Kim, M.-J. and Benner, S. A. (2015) High-throughput multiplexed xMAP Luminex array panel for detection of twenty two medically important mosquito-borne arboviruses based on innovations in synthetic biology, *J. Virol. Methods*, 214, 60-74.
5. Yaren, O., Alto, B. W., Gangodkar, P. V., Ranade, S. R., Patil, K. N., Bradley, K. M., Yang, Z. Y., Phadke, N. and Benner, S. A. (2017) Point of sampling detection of Zika virus within a multiplexed kit capable of detecting dengue and chikungunya. *BMC Infect. Dis.*, 17.
6. De Bel, A., Marissens, D., Debaisieux, L., Liesnard, C., Van den Wijngaert, S., Lauwers, S. and Pierard, D. (2010) Correction of Underquantification of human is immunodeficiency virus Type 1 Load with the Second Version of the Roche COBAS AmpliPrep/COBAS TaqMan Assay. *J. Clin. Microbiol.*, 1337-1342.
7. Young, T. P., Napolitano, Paquet, A. C., Parkin, N. T., Fransen, S., Trinh, R., Haddad, M., Hackett, J., Jr. and Cloherty, G. A. (2013) Minimal sequence variability of the region of HIV-1 integrase targeted by the Abbott RealTime HIV-1 viral load assay in clinical specimens with reduced susceptibility to raltegravir. *J. Virol. Methods*, 193, 693-696.
8. Liang, F., Liu, Y.-Z. and Zhang, P. (2013) Universal base analogues and their applications in DNA sequencing technology. *RSC Advances*, 3, 14910-14928.
9. Loakes, D. (2001) The applications of universal DNA base analogues, *Nucelic Acids Res.*, 29, 2437-2447.
10. Ingale, S. A. Leonard P., Yang, H. Z., and Seela, F. (2014) 5-Nitroindole oligoncleotides with alkynyl side chains: universal base pairing, triple bond hydration and properties of pyrene "click" adducts. *Org. Chem.*, 12, 8519-8532).
11. Petrie, K. L. and Joyce, G. F. (2010) Deep sequencing analysis of mutations resulting from the incorporation of dNTP analogs. *Nucleic Acids Res.*, 38, 8095-8104.
12. Day, J. P., Bergstrom, D., Hammer, R. P. and Barany, F. (1999) Nucleotide analogs facilitate base conversion with 3' mismatch primers. *Nucleic Acids Res*, 27, 1810-1818.
13. Zheng, L. D,. Gibbs, M. J. and Rodoni, B. C. (2008) Quantitative PCR measurements of the effects of introducing inosines into primers provides guidelines for improved degenerate primer design. *J Virol. Methods*, 153, 97-103.
14. Li, Y. Z., Zhao, P. Zhang, M. D., Zhao, X. Y. and Li, X. Y. (2013) Multistep DNA-Templated Synthesis Using a Universal Template. *J. Am. Chem. Soc.*, 35, 17727-17730.
15. Watkins, N. E. and SantaLucia, J. (2005) Nearest-neighbor thermodynamics of deoxyinosine pairs in DNA duplexes. *Nucleic Acids Res.*, 33, 6258-6267.
16. Vorobiev, A. V., Scarr, N. K., Belousov, Y. and Lukhtanov, E. A. (2013) 7-Aminobutynyl-8-aza-7-deazahypoxanthine as a quasi-universal nucleobase. *Nucleosides Nucleotides & Nucleic Acids*, 32, 421-438.
17. Stoltzfus, A. and Norris, R. W. (2016) On the causes of evolutionary transition:transversion Bias. *Mol. Biol. Evol.* 33, 595-602.
18. Collins, D. W. and Jukes, T. H. (1994) Coding sequences since the human-rodent divergence. *Genomics*, 20, 386-396.
19. LaPointe, S. M., Wheaton, C. A. and Wetmore, S. D. (2004) The degenerate properties of modified purine and pyrimidine DNA bases: A density functional study. *Chem. Phys. Lett.*, 400, 487-493.
20. Lin, P. K. T. and Brown, D. M. (1989) Synthesis and duplex stability of oligonucleotides containing cytosine-thymine analogs, *Nucleic Acids Res*, 17, 10373-10383.
21. Brown, D. M. and Lin, P. K. T. (1991) Synthesis and duplex stability of oligonucleotides containing adenine guanine analogs. *Carbohydrate Res*, 216, 129-139.
22. Kamiya, H., Muratakamiya, N., Lin, P. K. T., Brown, D. M., and Ohtsuka, E. (1994) Nucleotide incorporation opposite degenerate bases by taq DNA-polynaerase. *Nucleosides & Nucleotides*, 13, 1483-1492.
23. Williams, D. M., Loakes, D. and Brown, D. M. (1998) Synthesis of a hydrogen-bond-degenerate tricyclic pyrrolopyrimidine nucleoside and of its 5'-triphosphate. *J. Chem. Soc.-Perkin Trans.* 1, 21, 3565-3570.
24. Williams, D. M., Yakovlev, D. Y. and Brown, D. M. (1997) The synthesis of a tricyclic pyrrolopyrimidine related to N-6-hydroxyadenine. *J. Chem Soc.-Perkin Trans.* 1, 8, 1171-1178.

25. Angelov, T. Guainazzi, A. and Schärer, O. D. (2009) Generation of DNA Interstrand Cross-Links by Post-Synthetic Reductive Amination *Org. Lett.* 11, 661-664.

26. Hill, F., Loakes, D. and Brown, D. M. (1998) Polymerase recognition of synthetic oligodeoxyribonucleotides incorporating degenerate pyrimidine and purine bases. *Proc. Natl. Acad. Sci. U.S.A.*, 95, 4258-4263.

27. LaPointe, S. M., Wheaton, C. A. and Wetmore, S. D. (2004) The degenerate properties of modified purine and pyrimidine DNA bases. *Chem. Phys. Lett.*, 400, 487-493.

28. Colucci, G.; Knobel, R. (2011) The COBAS (R) TaqMan (R) hepatitis C virus assays: automated systems for accurate and sensitive viral load quantification. *Expert Rev. Molecular Diagnostics* 11, 793-798.

29. Macleod I. J., Rowley C. F. and Essex M. (2015) Methods of determining polymorphisms. WO 2015/048730.

What is claimed is:

1. A process for ligating a donor fragment and an acceptor fragment together, said fragments being DNA, RNA or DNA-RNA oligonucleotides, said process comprising (a) contacting said fragments with a DNA or RNA template that comprises two adjacent segments to form a complex, a first segment that is 5'-adjacent to a second segment, wherein said first segment is substantially complementary to the donor fragment that carries a 5'-phosphate group, and said second segment is substantially complementary to the acceptor fragment, under conditions where said donor fragment binds to form a duplex with said first segment, and said acceptor fragment binds to form a duplex with said second segment, and (b) incubating said complex with a ligase under conditions where the two fragments become joined by a phosphodiester bond, wherein said duplexes contain at least one nucleobase pair selected from the group consisting of

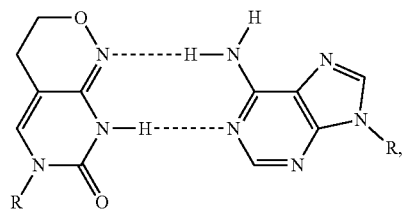

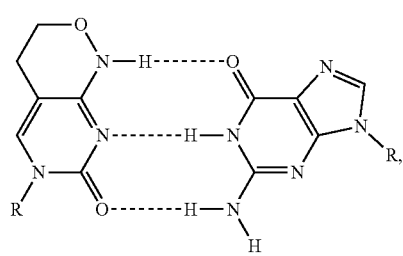

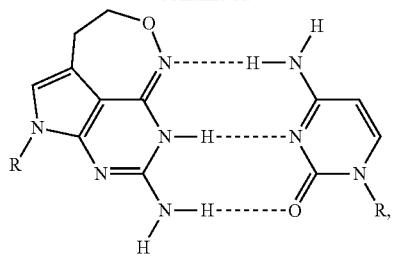

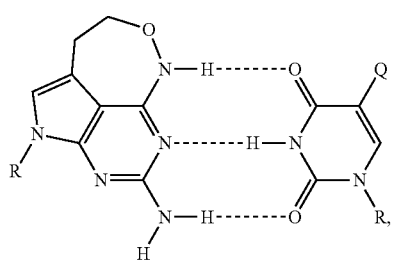

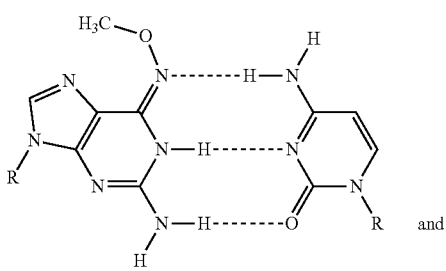

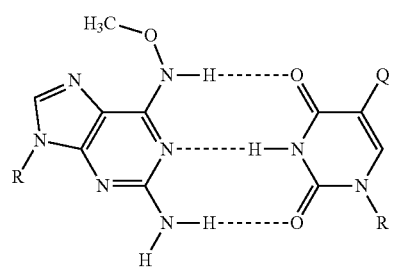

wherein Q is either CH₃ or H, and R is the point of attachment of the heterocycle nucleobase to the rest of the oligonucleotide.

2. The process of claim 1 wherein said ligase is the *Thermus aquaticus* DNA ligase, 9° N DNA ligase, Pfu DNA ligase, T4 DNA ligase, Splint R® ligase, T4 RNA ligase, or High Fidelity Taq DNA ligase.

3. The process of claim 1 wherein both of said duplexes contain at least one nucleobase pair selected from the group consisting of

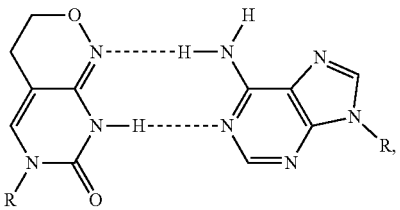

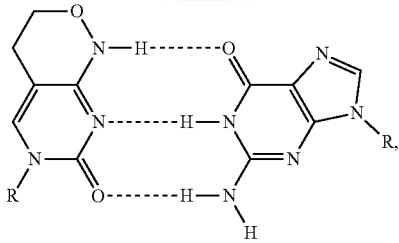

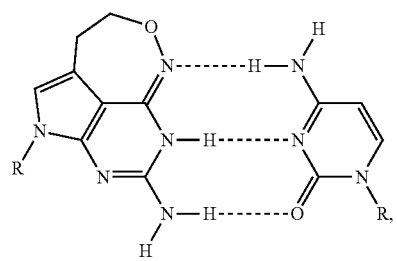

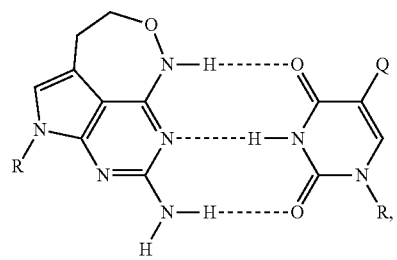

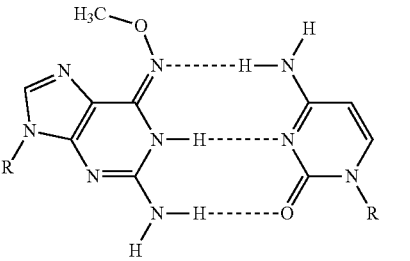

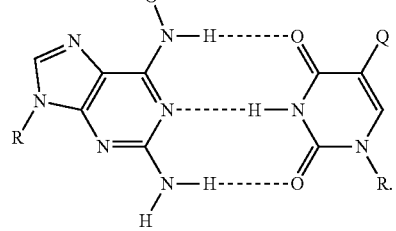

4. The process of claim 1 wherein both of said duplexes contain multiple nucleobase pairs selected from the group consisting of

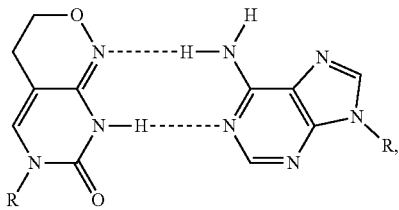

-continued

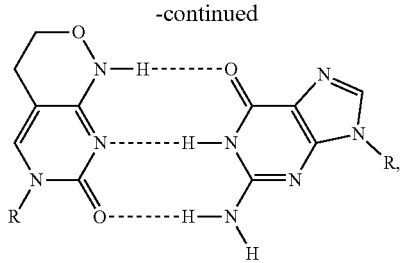

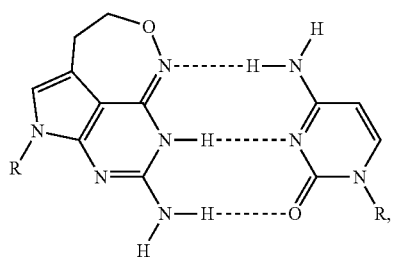

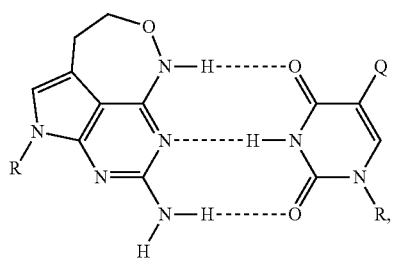

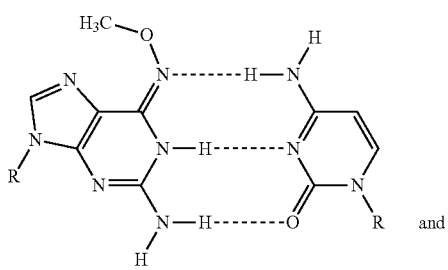

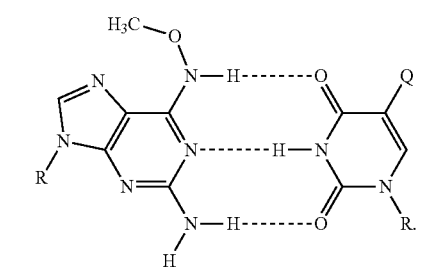

5. The process of claim 1, where multiple fragments are ligated on a template that contains multiple adjacent segments.

6. A process for synthesizing a DNA molecule that is complementary to a preselected template, said process comprising
(a) annealing said template to a DNA OR RNA primer and probe that is substantially complementary to a segment of said template to form a duplex, and
(b) incubating said duplex with a DNA polymerase and 2'-deoxynucleoside triphosphates under conditions where said primer is extended, wherein said primer includes at least one nucleotide comprising the heterocycle

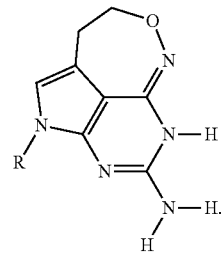

7. The process of claim 6, wherein said polymerase is Taq DNA polymerase, reverse transcriptase, or AmpliTaq Gold DNA polymerase.

8. The process of claim 6 wherein said primer includes at least two nucleotides comprising the heterocycle

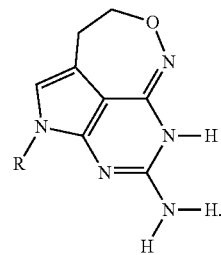

9. The process of claim 6 wherein said probe includes at least one nucleotides comprising the heterocycle

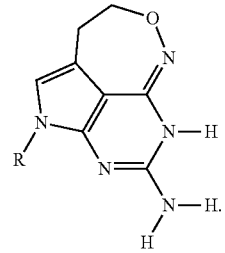

10. A process for increasing the number of copies of two complementary DNA target strands, wherein said process comprises:
(a) adding one or both of said target strands to an aqueous mixture that comprises a DNA polymerase, wherein
(b) said mixture also contains 2'-deoxynucleoside triphosphates that complement each nucleotide in said complementary DNA strands, wherein
(c) said aqueous mixture also contains primers comprising a first primer that is substantially complementary in sequence to a segment at or near the 3'-end of the first of said DNA strands, and a second primer that is substantially complementary in sequence to a segment at or near the 3'-end of the second of said DNA strands, and wherein at least one primer comprises at least one nucleotide comprising the heterocycle

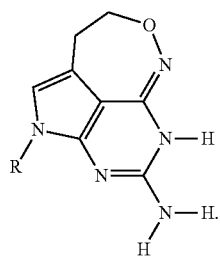

11. The process of claim 10 wherein one or both of said target strands is RNA.

12. The process of claim 10 wherein at least one primer comprises at least two nucleotides comprising the heterocycle

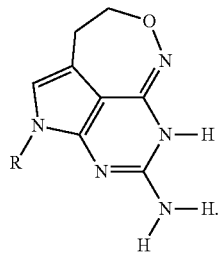

13. The process of claim 10, wherein said polymerase is Taq DNA polymerase, KlenTaq DNA polymerase, or AmpliTaq Gold DNA polymerase.

14. A process for determining what nucleotide occupies a site in a DNA target molecule, said process comprising
  (a) contacting said target sequence with a probe that is substantially complementary to the target sequence to form a complex, said probe containing a single ribonucleotide complementary to a nucleotide that might occupy said site, the remainder of the nucleotides in said probe being 2'-deoxyribonucleotides, under conditions where said probe and said target hybridize to form a duplex, and
  (b) incubating said complex with a ribonuclease H under conditions where the probe is cleaved should the probe ribonucleotide perfectly match the nucleotide in said site, wherein said duplexes contains at least one nucleobase pair selected from the group consisting of

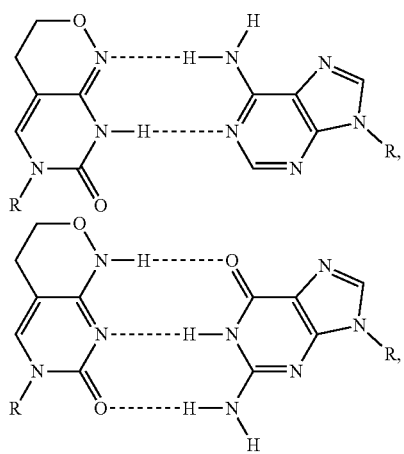

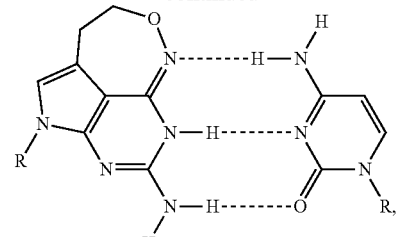

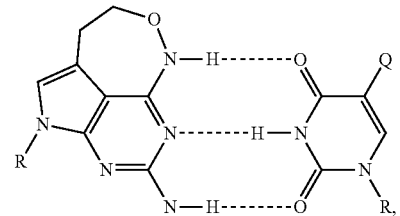

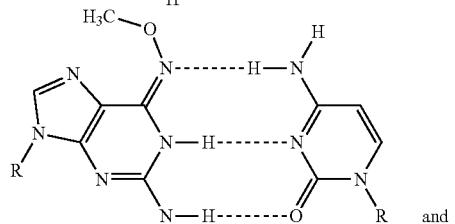

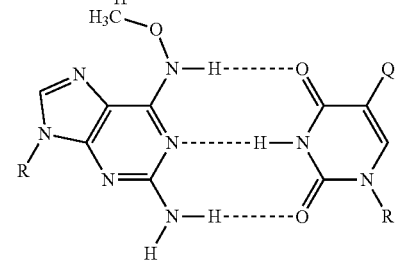

wherein Q is either $CH_3$ or H, and R is the point of attachment of the heterocycle nucleobase to the rest of the oligonucleotide.

15. The process of claim 14 wherein said ribonuclease H is ribonuclease H2.

16. The process of claim 14 wherein said duplexes contains at least two nucleobase pairs selected from the group consisting of

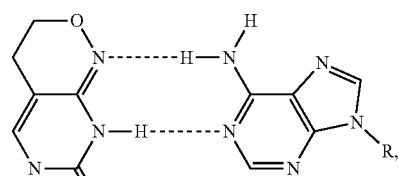

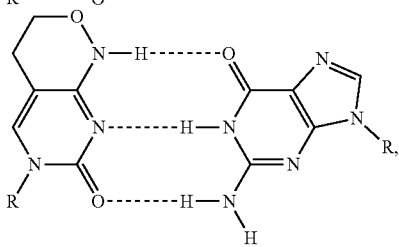

63
-continued
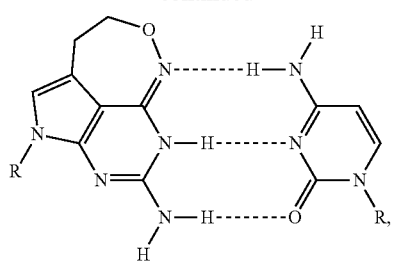
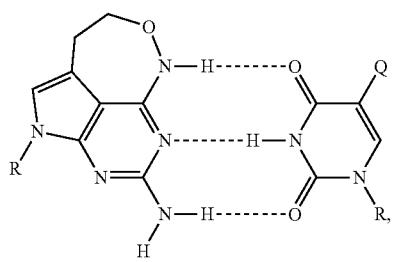
64
-continued
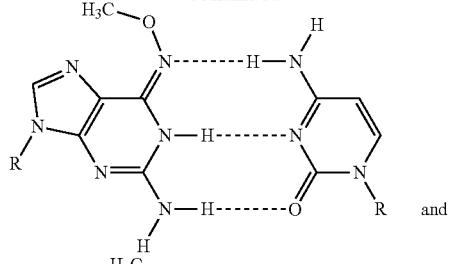
and
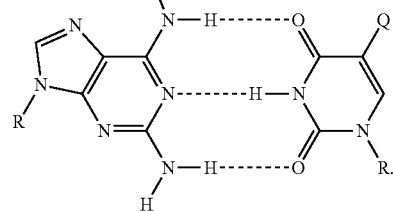
* * * * *

SEQUENCE LISTING

```
<160> NUMBER OF SEQ ID NOS: 72

<210> SEQ ID NO 1
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (15)..(15)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

<400> SEQUENCE: 1
gagtctcgac anagntccca gagg                                              24

<210> SEQ ID NO 2
<211> LENGTH: 24
<212> TYPE: DNA
<213> ORGANISM: Artificial Sequence
<220> FEATURE:
<223> OTHER INFORMATION: synthetic

<400> SEQUENCE: 2
cctctgggac ctctgtcgag actc                                              24

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
cctctgggat ctttgtcgag actc                                              24

<210> SEQ ID NO 4
<211> LENGTH: 24
<212> TYPE: DNA
<213> ORGANISM: Artificial Sequence
<220> FEATURE:
<223> OTHER INFORMATION: synthetic

<400> SEQUENCE: 4
cctctgggag ctgtgtcgag actc                                              24

<210> SEQ ID NO 5
<211> LENGTH: 24
<212> TYPE: DNA
<213> ORGANISM: Artificial Sequence
<220> FEATURE:
<223> OTHER INFORMATION: synthetic
```

```
<400> SEQUENCE: 5
cctctgggaa ctatgtcgag actc                                              24

<210> SEQ ID NO 6
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: 2-amino-6-methoxyaminopurine
<220> FEATURE:
<221> NAME/KEY: misc_feature
<222> LOCATION: (15)..(15)
<223> OTHER INFORMATION: 2-amino-6-methoxyaminopurine

<400> SEQUENCE: 6
gagtctcgac anagntccca gagg                                              24

<210> SEQ ID NO 7
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: inosin
<220> FEATURE:
<221> NAME/KEY: misc_feature
<222> LOCATION: (15)..(15)
<223> OTHER INFORMATION: inosin

<400> SEQUENCE: 7
gagtctcgac anagntccca gagg                                              24

<210> SEQ ID NO 8
<211> LENGTH: 24
<212> TYPE: DNA
<213> ORGANISM: Artificial Sequence
<220> FEATURE:
<223> OTHER INFORMATION: synthetic

<400> SEQUENCE: 8
gagtctcgac agaggtccca gagg                                              24

<210> SEQ ID NO 9
<211> LENGTH: 24
<212> TYPE: DNA
<213> ORGANISM: Artificial Sequence
<220> FEATURE:
<223> OTHER INFORMATION: synthetic

<400> SEQUENCE: 9
gagtctcgac aaagatccca gagg                                              24

<210> SEQ ID NO 10
<211> LENGTH: 24
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (3)..(3)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (21)..(21)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

<400> SEQUENCE: 10
gantctcgac agagatccca nagg                                           24

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
cctctgggat ctctgtcgag actc                                           24

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
cctttgggat ctttgtcgag attc                                           24

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
cctgtgggag ctgtgtcgag agtc                                           24

<210> SEQ ID NO 14
<211> LENGTH: 24
<212> TYPE: DNA
<213> ORGANISM: Artificial Sequence
<220> FEATURE:
<223> OTHER INFORMATION: synthetic

<400> SEQUENCE: 14
cctatgggaa ctatgtcgag aatc                                           24

<210> SEQ ID NO 15
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: 2-amino-6-methoxyaminopurine
<220> FEATURE:
<221> NAME/KEY: misc_feature
<222> LOCATION: (21)..(21)
<223> OTHER INFORMATION: 2-amino-6-methoxyaminopurine
```

<400> SEQUENCE: 15
gantctcgac agagatccca nagg                                          24

<210> SEQ ID NO 16
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (3)..(3)
<223> OTHER INFORMATION: inosin
<220> FEATURE:
<221> NAME/KEY: misc_feature
<222> LOCATION: (21)..(21)
<223> OTHER INFORMATION: inosin

<400> SEQUENCE: 16
gantctcgac agagatccca nagg                                          24

<210> SEQ ID NO 17
<211> LENGTH: 24
<212> TYPE: DNA
<213> ORGANISM: Artificial Sequence
<220> FEATURE:
<223> OTHER INFORMATION: synthetic

<400> SEQUENCE: 17
gaatctcgac aaagatccca aagg                                          24

<210> SEQ ID NO 18
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (15)..(15)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (21)..(21)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene

<400> SEQUENCE: 18
gagtctcgnc agagntccca nagg                                          24

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
cctctgggac ctctgccgag actc                                          24

```
<210> SEQ ID NO 20
<211> LENGTH: 24
<212> TYPE: DNA
<213> ORGANISM: Artificial Sequence
<220> FEATURE:
<223> OTHER INFORMATION: synthetic

<400> SEQUENCE: 20
cctttgggat ctctgtcgag actc                                          24

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
cctgtgggag ctctggcgag actc                                          24

<210> SEQ ID NO 22
<211> LENGTH: 24
<212> TYPE: DNA
<213> ORGANISM: Artificial Sequence
<220> FEATURE:
<223> OTHER INFORMATION: synthetic

<400> SEQUENCE: 22
cctatgggaa ctctgacgag actc                                          24

<210> SEQ ID NO 23
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: 2-amino-6-methoxyaminopurine
<220> FEATURE:
<221> NAME/KEY: misc_feature
<222> LOCATION: (15)..(15)
<223> OTHER INFORMATION: 2-amino-6-methoxyaminopurine
<220> FEATURE:
<221> NAME/KEY: misc_feature
<222> LOCATION: (21)..(21)
<223> OTHER INFORMATION: 2-amino-6-methoxyaminopurine

<400> SEQUENCE: 23
gagtctcgnc agagntccca nagg                                          24

<210> SEQ ID NO 24
<211> LENGTH: 24
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (9)..(9)
<223> OTHER INFORMATION: inosin
<220> FEATURE:
<221> NAME/KEY: misc_feature
<222> LOCATION: (15)..(15)
<223> OTHER INFORMATION: inosin
<220> FEATURE:
<221> NAME/KEY: misc_feature
<222> LOCATION: (21)..(21)
<223> OTHER INFORMATION: inosin
```

<400> SEQUENCE: 24
gagtctcgnc agagntccca nagg                                              24

<210> SEQ ID NO 25
<211> LENGTH: 24
<212> TYPE: DNA
<213> ORGANISM: Artificial Sequence
<220> FEATURE:
<223> OTHER INFORMATION: synthetic

<400> SEQUENCE: 25
gagtctcggc agaggtccca gagg                                              24

<210> SEQ ID NO 26
<211> LENGTH: 24
<212> TYPE: DNA
<213> ORGANISM: Artificial Sequence
<220> FEATURE:
<223> OTHER INFORMATION: synthetic

<400> SEQUENCE: 26
gagtctcgac agagatccca aagg                                              24

<210> SEQ ID NO 27
<211> LENGTH: 28
<212> TYPE: DNA
<213> ORGANISM: Artificial Sequence
<220> FEATURE:
<223> OTHER INFORMATION: synthetic

<400> SEQUENCE: 27
tgggaagttc aataaggaat accacatc                                          28

<210> SEQ ID NO 28
<211> LENGTH: 27
<212> TYPE: DNA
<213> ORGANISM: Artificial Sequence
<220> FEATURE:
<223> OTHER INFORMATION: synthetic

<400> SEQUENCE: 28
tgaaaaatat gcatcaccta catccag                                           27

<210> SEQ ID NO 29
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: 2-(2-Deoxy-b-D-ribofuranosyl)-4-pivaloylamino-
    2,6,8,9-tetrahydro-7-oxa-2,3,5,6-tetraazabenz[cd]azulene
<220> FEATURE:
<221> NAME/KEY: misc_feature
<222> LOCATION: (18)..(18)
<223> OTHER INFORMATION: 2-(2-Deoxy-b-D-ribofuranosyl)-4-pivaloylamino-
    2,6,8,9-tetrahydro-7-oxa-2,3,5,6-tetraazabenz[cd]azulene
<220> FEATURE:
<221> NAME/KEY: misc_feature
<222> LOCATION: (24)..(24)
<223> OTHER INFORMATION: 2-(2-Deoxy-b-D-ribofuranosyl)-4-pivaloylamino-
    2,6,8,9-tetrahydro-7-oxa-2,3,5,6-tetraazabenz[cd]azulene

<400> SEQUENCE: 29
tgggaagttc antaaggnat accncatc                                          28

```
<210> SEQ ID NO 30
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (22)..(22)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (26)..(26)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

<400> SEQUENCE: 30
tgaaaaatat gcatcnccta cntccng                                         27

<210> SEQ ID NO 31
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (12)..(12)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (18)..(18)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (24)..(24)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

<400> SEQUENCE: 31
tgggangttc antaaggnat accncatc                                        28

<210> SEQ ID NO 32
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (16)..(16)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
```

```
<220> FEATURE:
<221> NAME/KEY: misc_feature
<222> LOCATION: (22)..(22)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (26)..(26)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

<400> SEQUENCE: 32
tgaaaantat gcatcnccta cntccng                                        27

<210> SEQ ID NO 33
<211> LENGTH: 28
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (6)..(6)
<223> OTHER INFORMATION: 2-amino-6-methoxyaminopurine
<220> FEATURE:
<221> NAME/KEY: misc_feature
<222> LOCATION: (12)..(12)
<223> OTHER INFORMATION: 2-amino-6-methoxyaminopurine
<220> FEATURE:
<221> NAME/KEY: misc_feature
<222> LOCATION: (18)..(18)
<223> OTHER INFORMATION: 2-amino-6-methoxyaminopurine
<220> FEATURE:
<221> NAME/KEY: misc_feature
<222> LOCATION: (24)..(24)
<223> OTHER INFORMATION: 2-amino-6-methoxyaminopurine

<400> SEQUENCE: 33
tgggangttc antaaggnat accncatc                                       28

<210> SEQ ID NO 34
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 2-amino-6-methoxyaminopurine
<220> FEATURE:
<221> NAME/KEY: misc_feature
<222> LOCATION: (16)..(16)
<223> OTHER INFORMATION: 2-amino-6-methoxyaminopurine
<220> FEATURE:
<221> NAME/KEY: misc_feature
<222> LOCATION: (22)..(22)
<223> OTHER INFORMATION: 2-amino-6-methoxyaminopurine
<220> FEATURE:
<221> NAME/KEY: misc_feature
<222> LOCATION: (26)..(26)
<223> OTHER INFORMATION: 2-amino-6-methoxyaminopurine

<400> SEQUENCE: 34
tgaaaantat gcatcnccta cntccng                                        27

<210> SEQ ID NO 35
<211> LENGTH: 28
<212> TYPE: DNA
<213> ORGANISM: Artificial Sequence
<220> FEATURE:
<223> OTHER INFORMATION: synthetic
```

```
<220> FEATURE:
<221> NAME/KEY: misc_feature
<222> LOCATION: (6)..(6)
<223> OTHER INFORMATION: inosin
<220> FEATURE:
<221> NAME/KEY: misc_feature
<222> LOCATION: (12)..(12)
<223> OTHER INFORMATION: inosin
<220> FEATURE:
<221> NAME/KEY: misc_feature
<222> LOCATION: (18)..(18)
<223> OTHER INFORMATION: inosin
<220> FEATURE:
<221> NAME/KEY: misc_feature
<222> LOCATION: (24)..(24)
<223> OTHER INFORMATION: inosin

<400> SEQUENCE: 35
tgggangttc antaaggnat accncatc                                           28

<210> SEQ ID NO 36
<211> LENGTH: 27
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: inosin
<220> FEATURE:
<221> NAME/KEY: misc_feature
<222> LOCATION: (16)..(16)
<223> OTHER INFORMATION: inosin
<220> FEATURE:
<221> NAME/KEY: misc_feature
<222> LOCATION: (22)..(22)
<223> OTHER INFORMATION: inosin
<220> FEATURE:
<221> NAME/KEY: misc_feature
<222> LOCATION: (26)..(26)
<223> OTHER INFORMATION: inosin

<400> SEQUENCE: 36
tgaaaantat gcatcnccta cntccng                                            27

<210> SEQ ID NO 37
<211> LENGTH: 90
<212> TYPE: DNA
<213> ORGANISM: Artificial Sequence
<220> FEATURE:
<223> OTHER INFORMATION: synthetic

<400> SEQUENCE: 37
tgggaagttc aataaggaat accacatccc gcagggttaa aaagaaaaa atcagtaaca          60 gtactggatg taggtgatgc atattttca                                          90

<210> SEQ ID NO 38
<211> LENGTH: 90
<212> TYPE: DNA
<213> ORGANISM: Artificial Sequence
<220> FEATURE:
<223> OTHER INFORMATION: synthetic

<400> SEQUENCE: 38
tgggaggttc agtaagggat accgcatccc gcagggttaa aaagaaaaa atcagtaaca          60 gtaccggacg taggcgatgc atacttttca                                         90
```

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
tctgaaatct actaattttc                                           20

<210> SEQ ID NO 40
<211> LENGTH: 32
<212> TYPE: DNA
<213> ORGANISM: Artificial Sequence
<220> FEATURE:
<223> OTHER INFORMATION: synthetic

<400> SEQUENCE: 40
tcccagaagt cttgagttct cttattaagt tc                             32

<210> SEQ ID NO 41
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-6-methoxyaminopurine
<220> FEATURE:
<221> NAME/KEY: misc_feature
<222> LOCATION: (7)..(7)
<223> OTHER INFORMATION: 2-amino-6-methoxyaminopurine

<400> SEQUENCE: 41
tctnaantct actaattttc                                           20

<210> SEQ ID NO 42
<211> LENGTH: 32
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: 2-amino-6-methoxyaminopurine
<220> FEATURE:
<221> NAME/KEY: misc_feature
<222> LOCATION: (24)..(24)
<223> OTHER INFORMATION: 2-amino-6-methoxyaminopurine
<220> FEATURE:
<221> NAME/KEY: misc_feature
<222> LOCATION: (29)..(29)
<223> OTHER INFORMATION: 2-amino-6-methoxyaminopurine

<400> SEQUENCE: 42
tcccagaagt cttganttct cttnttaant tc                             32

<210> SEQ ID NO 43
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-amino-6-methoxyaminopurine

```
<220> FEATURE:
<221> NAME/KEY: misc_feature
<222> LOCATION: (7)..(7)
<223> OTHER INFORMATION: 2-amino-6-methoxyaminopurine
<220> FEATURE:
<221> NAME/KEY: misc_feature
<222> LOCATION: (11)..(11)
<223> OTHER INFORMATION: 2-amino-6-methoxyaminopurine
<220> FEATURE:
<221> NAME/KEY: misc_feature
<222> LOCATION: (15)..(15)
<223> OTHER INFORMATION: 2-amino-6-methoxyaminopurine

<400> SEQUENCE: 43
tctnaantct nctantttc                                                20

<210> SEQ ID NO 44
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (7)..(7)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene

<400> SEQUENCE: 44
tctnaantct actaattttc                                               20

<210> SEQ ID NO 45
<211> LENGTH: 32
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (24)..(24)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (29)..(29)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene

<400> SEQUENCE: 45
tcccagaagt cttganttct cttnttaant tc                                 32

<210> SEQ ID NO 46
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
```

<220> FEATURE:
<221> NAME/KEY: misc_feature
<222> LOCATION: (7)..(7)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (11)..(11)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene
<220> FEATURE:
<221> NAME/KEY: misc_feature
<222> LOCATION: (15)..(15)
<223> OTHER INFORMATION: 2-(2-Deoxy-b-D-ribofuranosyl)-4-pivaloylamino-
     2,6,8,9-tetrahydro-7-oxa-2,3,5,6-tetraazabenz[cd]azulene

<400> SEQUENCE: 46
tctnaantct nctantttc                                              20

<210> SEQ ID NO 47
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: inosin
<220> FEATURE:
<221> NAME/KEY: misc_feature
<222> LOCATION: (7)..(7)
<223> OTHER INFORMATION: inosin
<220> FEATURE:
<221> NAME/KEY: misc_feature
<222> LOCATION: (11)..(11)
<223> OTHER INFORMATION: inosin
<220> FEATURE:
<221> NAME/KEY: misc_feature
<222> LOCATION: (15)..(15)
<223> OTHER INFORMATION: inosin

<400> SEQUENCE: 47
tctnaantct nctantttc                                              20

<210> SEQ ID NO 48
<211> LENGTH: 32
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (16)..(16)
<223> OTHER INFORMATION: inosin
<220> FEATURE:
<221> NAME/KEY: misc_feature
<222> LOCATION: (24)..(24)
<223> OTHER INFORMATION: inosin
<220> FEATURE:
<221> NAME/KEY: misc_feature
<222> LOCATION: (29)..(29)
<223> OTHER INFORMATION: inosin

<400> SEQUENCE: 48
tcccagaagt cttganttct cttnttaant tc                               32

<210> SEQ ID NO 49
<211> LENGTH: 52
<212> TYPE: DNA
<213> ORGANISM: Artificial Sequence
<220> FEATURE:
<223> OTHER INFORMATION: synthetic

<400> SEQUENCE: 49
gaaaattagt agatttcaga gaacttaata agagaactca agacttctgg ga    52

<210> SEQ ID NO 50
<211> LENGTH: 52
<212> TYPE: DNA
<213> ORGANISM: Artificial Sequence
<220> FEATURE:
<223> OTHER INFORMATION: synthetic

<400> SEQUENCE: 50
gaaaattagt agactttaga gaatttaaca agagaactca agacttctgg ga    52

<210> SEQ ID NO 51
<211> LENGTH: 52
<212> TYPE: DNA
<213> ORGANISM: Artificial Sequence
<220> FEATURE:
<223> OTHER INFORMATION: synthetic

<400> SEQUENCE: 51
gaaaattagc agactttaga gaatttaaca agagaattca agacttctgg ga    52

<210> SEQ ID NO 52
<211> LENGTH: 20
<212> TYPE: DNA
<213> ORGANISM: Artificial Sequence
<220> FEATURE:
<223> OTHER INFORMATION: synthetic

<400> SEQUENCE: 52
tactgttact gattttttct    20

<210> SEQ ID NO 53
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: 2-amino-6-methoxyaminopurine
<220> FEATURE:
<221> NAME/KEY: misc_feature
<222> LOCATION: (5)..(5)
<223> OTHER INFORMATION: 2-amino-6-methoxyaminopurine
<220> FEATURE:
<221> NAME/KEY: misc_feature
<222> LOCATION: (11)..(11)
<223> OTHER INFORMATION: 2-amino-6-methoxyaminopurine

<400> SEQUENCE: 53
tnctnttact nattttttct    20

<210> SEQ ID NO 54
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (2)..(2)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

```
<220> FEATURE:
<221> NAME/KEY: misc_feature
<222> LOCATION: (5)..(5)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene
<220> FEATURE:
<221> NAME/KEY: misc_feature
<222> LOCATION: (11)..(11)
<223> OTHER INFORMATION: 2-(2-Deoxy-b-D-ribofuranosyl)-4-pivaloylamino-
      2,6,8,9-tetrahydro-7-oxa-2,3,5,6-tetraazabenz[cd]azulene

<400> SEQUENCE: 54
tnctnttact nattttttct                                                  20

<210> SEQ ID NO 55
<211> LENGTH: 47
<212> TYPE: DNA
<213> ORGANISM: Artificial Sequence
<220> FEATURE:
<223> OTHER INFORMATION: synthetic

<400> SEQUENCE: 55
agaaaaaatc agtaacagta ctggatgtag gtgatgcata tttttca                    47

<210> SEQ ID NO 56
<211> LENGTH: 47
<212> TYPE: DNA
<213> ORGANISM: Artificial Sequence
<220> FEATURE:
<223> OTHER INFORMATION: synthetic

<400> SEQUENCE: 56
agaaaaaatc agtaacagta ttggatgtag gtgatgcata tttttca                    47

<210> SEQ ID NO 57
<211> LENGTH: 47
<212> TYPE: DNA
<213> ORGANISM: Artificial Sequence
<220> FEATURE:
<223> OTHER INFORMATION: synthetic

<400> SEQUENCE: 57
agaaaaaatt agtaacagca ccggatgtag gcgatgcata tttttca                    47

<210> SEQ ID NO 58
<211> LENGTH: 47
<212> TYPE: DNA
<213> ORGANISM: Artificial Sequence
<220> FEATURE:
<223> OTHER INFORMATION: synthetic

<400> SEQUENCE: 58
agaaaaaatt agtaacagca tcggatgtag gcgatgcata tttttca                    47

<210> SEQ ID NO 59
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (15)..(15)
<223> OTHER INFORMATION: ribonucleotide cytosine

<400> SEQUENCE: 59
ctcgtgaggt gatgnaggag atgggaggcg                                       30
```

```
<210> SEQ ID NO 60
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: inosin
<220> FEATURE:
<221> NAME/KEY: misc_feature
<222> LOCATION: (15)..(15)
<223> OTHER INFORMATION: ribonucleotide cytosine
<220> FEATURE:
<221> NAME/KEY: misc_feature
<222> LOCATION: (17)..(17)
<223> OTHER INFORMATION: inosin

<400> SEQUENCE: 60
ctcgtgaggt gntgnangag atgggaggcg                                    30

<210> SEQ ID NO 61
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: 2-amino-6-methoxyaminopurine
<220> FEATURE:
<221> NAME/KEY: misc_feature
<222> LOCATION: (15)..(15)
<223> OTHER INFORMATION: ribonucleotide cytosine
<220> FEATURE:
<221> NAME/KEY: misc_feature
<222> LOCATION: (17)..(17)
<223> OTHER INFORMATION: 2-amino-6-methoxyaminopurine

<400> SEQUENCE: 61
ctcgtgaggt gntgnangag atgggaggcg                                    30

<210> SEQ ID NO 62
<211> LENGTH: 30
<212> TYPE: DNA
<213> ORGANISM: Artificial Sequence
<220> FEATURE:
<223> OTHER INFORMATION: synthetic

<400> SEQUENCE: 62
cgcctcccat ctcctgcatc acctcacgag                                    30

<210> SEQ ID NO 63
<211> LENGTH: 30
<212> TYPE: DNA
<213> ORGANISM: Artificial Sequence
<220> FEATURE:
<223> OTHER INFORMATION: synthetic

<400> SEQUENCE: 63
cgcctcccat ctcctacatc acctcacgag                                    30

<210> SEQ ID NO 64
<211> LENGTH: 30
<212> TYPE: DNA
<213> ORGANISM: Artificial Sequence
<220> FEATURE:
<223> OTHER INFORMATION: synthetic
```

<400> SEQUENCE: 64
cgcctcccat ctcttgcacc acctcacgag                                30

<210> SEQ ID NO 65
<211> LENGTH: 30
<212> TYPE: DNA
<213> ORGANISM: Artificial Sequence
<220> FEATURE:
<223> OTHER INFORMATION: synthetic

<400> SEQUENCE: 65
cgcctcccat ctcttacacc acctcacgag                                30

<210> SEQ ID NO 66
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (15)..(15)
<223> OTHER INFORMATION: ribonucleotide adenine

<400> SEQUENCE: 66
ctcgtgaggt gatgnaggag atgggaggcg                                30

<210> SEQ ID NO 67
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: inosin
<220> FEATURE:
<221> NAME/KEY: misc_feature
<222> LOCATION: (15)..(15)
<223> OTHER INFORMATION: ribonucleotide adenine
<220> FEATURE:
<221> NAME/KEY: misc_feature
<222> LOCATION: (17)..(17)
<223> OTHER INFORMATION: inosin

<400> SEQUENCE: 67
ctcgtgaggt gntgnangag atgggaggcg                                30

<210> SEQ ID NO 68
<211> LENGTH: 30
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (12)..(12)
<223> OTHER INFORMATION: 2-amino-6-methoxyaminopurine
<220> FEATURE:
<221> NAME/KEY: misc_feature
<222> LOCATION: (15)..(15)
<223> OTHER INFORMATION: ribonucleotide adenine
<220> FEATURE:
<221> NAME/KEY: misc_feature
<222> LOCATION: (17)..(17)
<223> OTHER INFORMATION: 2-amino-6-methoxyaminopurine

```
<400> SEQUENCE: 68
ctcgtgaggt gntgnangag atgggaggcg                              30

<210> SEQ ID NO 69
<211> LENGTH: 30
<212> TYPE: DNA
<213> ORGANISM: Artificial Sequence
<220> FEATURE:
<223> OTHER INFORMATION: synthetic

<400> SEQUENCE: 69
cgcctcccat ctccttcatc acctcacgag                              30

<210> SEQ ID NO 70
<211> LENGTH: 30
<212> TYPE: DNA
<213> ORGANISM: Artificial Sequence
<220> FEATURE:
<223> OTHER INFORMATION: synthetic

<400> SEQUENCE: 70
cgcctcccat ctcctccatc acctcacgag                              30

<210> SEQ ID NO 71
<211> LENGTH: 30
<212> TYPE: DNA
<213> ORGANISM: Artificial Sequence
<220> FEATURE:
<223> OTHER INFORMATION: synthetic

<400> SEQUENCE: 71
cgcctcccat ctctttcacc acctcacgag                              30

<210> SEQ ID NO 72
<211> LENGTH: 30
<212> TYPE: DNA
<213> ORGANISM: Artificial Sequence
<220> FEATURE:
<223> OTHER INFORMATION: synthetic

<400> SEQUENCE: 72
cgcctcccat ctcttccacc acctcacgag                              30
```